United States Patent [19]

Helting et al.

[11] Patent Number: 5,204,259
[45] Date of Patent: Apr. 20, 1993

[54] METHODS AND SYSTEMS FOR PRODUCING HIV ANTIGENS

[75] Inventors: Torsten B. Helting, La Jolla, Calif.; Hakan Drevin, Uppsala, Sweden; Michael F. Nunn, Solana Beach, Calif.

[73] Assignee: Pharmacia Genetic Engineering, Inc., La Jolla, Calif.

[21] Appl. No.: 344,237

[22] Filed: Apr. 26, 1989

Related U.S. Application Data

[63] Continuation-in-part of Ser. No. 191,229, May 6, 1988, abandoned, which is a continuation-in-part of Ser. No. 206,499, Jun. 13, 1988, abandoned, which is a continuation-in-part of Ser. No. 258,016, Oct. 14, 1988, abandoned.

[51] Int. Cl.$^5$ .............. C12N 1/21; C12N 15/49; C12N 15/62; C12N 15/70
[52] U.S. Cl. .............. 435/252.3; 435/5; 435/69.1; 435/69.3; 435/69.7; 435/172.3; 435/252.33; 435/320.1; 435/974; 536/23.72; 930/221; 935/23; 935/27; 935/38; 935/45; 935/47; 935/72; 935/73
[58] Field of Search .............. 435/69.1, 69.3, 320.1, 435/172.3, 252.3, 252.33; 536/27

[56] References Cited

U.S. PATENT DOCUMENTS

4,808,536  2/1989  Chang et al. .............. 435/5
4,925,784  5/1990  Crowl et al. .............. 435/5

FOREIGN PATENT DOCUMENTS

0187041  12/1985  European Pat. Off.
0227169  12/1986  European Pat. Off.
0307149   9/1988  European Pat. Off.
2188639   4/1986  United Kingdom.

OTHER PUBLICATIONS

J. G. Huisman et al. (1987) Vox Sanguinis 53:31–36.
P. Tijssen, "Practices and Theory of Enzyme Immunoassays", in *Laboratory Techniques in Biochemistry and Molecular Biology*, vol. 15, R. H. Burdon et al., ed. Elsevier, Amsterdam (1985), pp. 14–17, 470–471, 482–483.
N. T. Chang et al. (1985) Science 228: 93–96.
M. Guyader et al. (1987) Nature 326: 662–669.
Shoeman et al., *Analytical Biochemistry*, 161:370–379 (1987).
Ratner et al., Nature, 313:277–285 (1985).
Dowbenko et al., *Proc. Natl. Acad. Sci., U.S.A.*, 82:7748–7752 (1985).
Ghrayeb et al., *DNA*, 5(2):93–99 (1986).

*Primary Examiner*—Richard A. Schwartz
*Assistant Examiner*—Johnny F. Railey, II
*Attorney, Agent, or Firm*—Dressler, Goldsmith, Shore, Sutker & Milnamow, Ltd.

[57] ABSTRACT

The present invention relates to a DNA segment encoding a recombinant HIV p24 protein or HIV p24-gp41 fusion protein and a recombinant DNA (rDNA) molecule capable of expressing either protein. Cells transformed with the rDNA, methods for producing the fusion protein and diagnostic methods and systems using the fusion protein are also described.

12 Claims, 20 Drawing Sheets

```
                                                      MetProIleValGlnAsnIleGlnGlyGlnMet                11
AGGAGGGTTTTTCATATGCCAGAACATCGTGCAGAACATCCAGGGGCAAATG                                                   48

ValHisGlnAlaIleSerProArgThrLeuAsnAlaTrpValLysVal                                                       27
GTACATCAGGCCATATCACCTAGAACTTAAATGCATGGGTAAAAGTA                                                        96

ValGluGluLysAlaPheSerProGluValIleProMetPheSerAla                                                       43
GTAGAAGAGAAGGCTTTCAGCCCCAGAAGTGATACCCATGTTTTCAGCA                                                     144

LeuSerGluGlyAlaThrProGlnAspLeuAsnThrMetLeuAsnThr                                                       59
TTATCAGAAGGAGCCACCCCACAAGATTTAAACACCATGCTAAACACA                                                      192

ValGlyGlyHisGlnAlaAlaMetGlnMetLeuLysGluThrIleAsn                                                       75
GTGGGGGGACATCAAGCAGCCATGCAAATGTTAAAAGAGACCATCAAT                                                      240

GluGluAlaAlaGluTrpAspArgValHisProValHisAlaGlyPro                                                       91
GAGGAAGCTGCAGAATGGGATAGAGTGCATCCAGTGCATGCAGGGCCT                                                      288

IleAlaProGlyGlnMetArgGluProArgGlySerAspIleAlaGly                                                      107
ATTGCACCAGGCCAGATGAGAGAACCAAGGGGAAGTGACATAGCAGGA                                                      336
```

FIG. IA-1

```
ThrThrSerThrLeuGlnGluGlnIleGlyTrpMetThrAsnPro              123
ACTACTAGTACCCTTCAGGAACAAATAGGATGGATGACAAATAATCCA           384

ProIleProValGlyGluIleTryLysArgTrpIleIleLeuGlyLeu           139
CCTATCCCAGTAGGAGAAATTTATAAAGATGGATAATCCTGGGATTA            432

AsnLysIleValArgMetTyrSerProThrSerIleLeuAspIleArg           155
AATAAAATAGTAAGAATGTATAGCCCTACCAGCATTCTGGACATAAGA           480

GlnGlyProLysGluProPheArgAspTyrValAspArgPheTyrLys           171
CAAGGACCAAAGGAACCCTTTAGAGACTATGTAGACCGGTTCTATAAA           528

ThrLeuArgAlaGluGlnAlaSerGlnGluValLysAsnTrpMetThr           187
ACTCTAAGAGCCGAGCAAGCTTCACAGGAGGTAAAAAATTGGATGACA           576

GluThrLeuLeuValGlnAsnAlaAsnProAspCysLysThrIleLeu           203
GAAACCCTTGTTGGTCCAAAATGCGAACCCAGATTGTAAGACTATTTTA          624

LysAlaLeuGlyProAlaAlaThrLeuGluMetMetThrAlaCys              219
AAAGCATTGGGACCAGCGGCTACACTAGAAGAAATGATGACAGCATGT           672

GlnGlyValGlyGlyProGlyHisLysAlaArgValLeu                    232
CAGGGAGTAGGAGGACCCGGCCATAAGGCAAGAGTTTTGTAATAAG             718
```

FIG. IA-2

```
                                                         MetProIleValGlnAsnIleGlnGlyGlnMet         11
AGGAGGGTTTTCATATGCCAATCGTGCAGAACATCCAGGGGCAAATG                                                   48

ValHisGlnAlaIleSerProArgThrLeuAsnAlaTrpValLysVal                                                  27
GTACATCAGGCCATATCACCTAGAACTTTAAATGCATGGGTAAAAGTA                                                 96

ValGluGluLysAlaPheSerProGluValIleProMetPheSerAla                                                  43
GTAGAAGAGAAGGCTTTCAGCCCCAGAAGTGATACCCATGTTTTCAGCA                                                144

LeuSerGluGlyAlaThrProGlnAspLeuAsnThrMetLeuAsnThr                                                  59
TTATCAGAAGGAGCCACCCCACAAGATTTAAACACCATGCTAAACACA                                                 192

ValGlyGlyHisGlnAlaAlaMetGlnMetLeuLysGluThrIleAsn                                                  75
GTGGGGGGACATCAAGCAGCCATGCAAATGTTAAAAGAGACCATCAAT                                                 240

GluGluAlaAlaGluTrpAspArgValHisProValHisAlaGlyPro                                                  91
GAGGAAGCTGCAGAATGGGATAGAGTGCATCCAGTGCATGCAGGGCCT                                                 288

IleAlaProGlyGlnMetArgGluProArgGlySerAspIleAlaGly                                                 107
ATTGCACCAGGCCAGATGAGAGAACCAAGGGGAAGTGACATAGCAGGA                                                 336
```

FIG. IB-1

```
ThrThrSerThrLeuGluGlnIleGluGlnIleGlyTrpMetThrAsnPro          123
ACTACTAGTACCCTTCAGGAACAAATAGGATGGATGACAAATAATCCA              384

ProIleProValGlyGlyGluIleTrpLysArgTrpIleIleLeuGlyLeu          139
CCTATCCCAGTAGGAGAGAAATTTATAAAAGATGGATAATCCTGGATTA            432

AsnLysIleValArgMetTyrSerProThrSerIleLeuAspIleArg             155
AATAAAATAGTAAGAATGTATAGCCCTACCAGCATTCTGGACATAAGA              480

GlnGlyProLysGluProPheArgAspTyrValAspArgPheTyrLys             171
CAAGGACCAAAGGAACCCTTTAGAGACTATGTAGACCGGTTCTATAAA              528

ThrLeuArgAlaGluGluGlnAlaSerGlnAlaSerGlnAlaSerGlnLysAsnTrpMetThr    187
ACTCTAAGAGAGCAAGCTTCACAGGAGTAAAAAATTGGATGACA                  576

GluThrLeuLeuValGlnAsnAlaAsnProAspAspCysLysThrIleLeu          203
GAAACCTTGTTGGTCCAAAATGCGAACCCAGATTGTAAGACTATTTTA              624

LysAlaLeuGlyProAlaAlaThrLeuGluMetMetThrAlaCys                219
AAAGCATTGGGACCAGCGGCTACACTAGAGAAGAAATGATGACAGCATGT            672
```

FIG. 1B-2

```
GlnGlyValGlyGlyProAspGlnGlnLeuLeuGlyIleTrpGlyCys      235
CAGGGAGTAGGAGGACCAGACCAGCTGGGTATCTGGGCTGT             720

SerGlyLysLeuIleCysThrThrAlaValProTrpAsnGlyProGly      251
TCTGGCAAGCTGATCTGTACTACTGCTGTTCCCGTGGAACGGACCCGGC     768

HisLysAlaArgValLeu                                    257
CATAAGGCAAGAGTTTTGTAATAAG                             793
```

FIG. 1B-3

```
                                                          MetProIleValGlnAsnIleGlyGlnMet        11
                                          AGGAGGGTTTTCATATGCCAATCGTGCAGAACATCCAGGGGCAAATG        48

ValHisGlnAlaIleSerProArgThrLeuAsnAlaTrpValLysVal                                     27
           GTACATCAGGCCATATCACCTAGAACTTTAAATGCATGGGTAAAAGTA                                     96

ValGluGluLysAlaPheSerProGluValIleProMetPheSerAla                                     43
           GTAGAAGAGAAGGCTTTCAGCCCAGAAGTGATACCCATGTTTTCAGCA                                    144

LeuSerGluGlyAlaThrProGlnAspLeuAsnThrMetLeuAsnThr                                     59
           TTATCAGAAGGAGCCACCCCACAAGATTTAAACACCATGCTAAACACA                                    192

ValGlyGlyHisGlnAlaAlaMetGlnMetLeuLysGluThrIleAsn                                     75
           GTGGGGGACATCAAGCAGCCATGCAAATGTTAAAAGAGACCATCAAT                                     240

GluGluAlaAlaGluTrpAspArgValHisProValHisAlaGlyPro                                     91
           GAGGAAGCTGCAGAATGGGATAGAGTGCATCCAGTGCATGCAGGGCCT                                    288

IleAlaProGlyGlnMetArgGluProArgGlySerAspIleAlaGly                                    107
           ATTGCACCAGGCCAGATGAGAGAACCAAGGGGAAGTGACATAGCAGGA                                    336
```

FIG. IC-1

```
ThrThrSerThrLeuGlnIleGluGlnIleGlyTrpMetThrAsnPro    123
ACTACTAGTACCCCTTCAGGAACAAATAGGATGGATGACAAATAATCCA    384

ProIleProValGlyGluIleTrpLysArgTrpIleIleLeuGlyLeu    139
CCTATCCCAGTAGGAGAGAAATTTATAAAGATGGATAATCCTGGGATTA    432

AsnLysIleValArgMetTyrSerProThrSerIleLeuAspIleArg    155
AATAAAATAGTAAGAATGTATAGCCCTACCAGCCATTCTGGACATAAGA    480

GlnGlyProLysGluProPheArgAspTyrValAspArgPheTyrLys    171
CAAGGACCAAAGGAACCCTTTAGAGACTATGTAGACCGGTTCTATAAA    528

ThrLeuArgAlaGluGlnAlaSerGlnGluValLysAsnTrpMetThr    187
ACTCTAAGAGCCGAGCAAGCTTCACAGGAGGTAAAAAATTGGATGACA    576

GluThrLeuLeuValGlnAsnAlaAsnProAspCysLysThrIleLeu    203
GAAACCTTGTTGGTCCAAAATGCGAACCCAGATTGTAAGACTATTTTA    624

LysAlaLeuGlyProAlaAlaThrLeuGluMetMetThrAlaCys    219
AAAGCATTGGGACCAGCGGCTACACTAGAAGAAATGATGACAGCATGT    672
```

FIG. IC-2

```
GlnGlyValGlyGlyProAspGlnAlaArgLeuAsnSerTrpGlyCys      235
CAGGGAGTAGGAGGACCAGAGGCTCGTCTGAACTCCTGGGGTTGC         720

AlaPheArgGlnValCysHisThrThrValProTrpValAsnGlyPro      251
GCTTTCCGTCAGGTTTGCCACACCACCGTTCCGTGGGTTAACGGACCC      768

GlyHisLysAlaArgValLeu                                 258
GGCCATAAGGCAAGAGTTTTGTAATAAG                          796
```

FIG. IC-3

```
                    MetProIleValGlnAsnIleGlnGlyGlnMet                              11
AGGAGGGTTTTCATATGCCAATCGTGCAGAACATCCAGGGGCAAATG                                   48

ValHisGlnAlaIleSerProArgThrLeuAsnAlaTrpValLysVal                                  27
GTACATCAGGCCATATCACCTAGAACTTTAAATGCATGGGTAAAAGTA                                  96

ValGluGluLysAlaPheSerProGluValIleProMetPheSerAla                                  43
GTAGAAGAGAAGGCTTTCAGCCCAGAAGTGATACCCATGTTTTCAGCA                                 144

LeuSerGluGlyAlaThrProGlnAspLeuAsnThrMetLeuAsnThr                                  59
TTATCAGAAGGAGCCACCCCACAAGATTTAAACACCATGCTAAACACA                                 192

ValGlyGlyHisGlnAlaMetLeuLysGluThrIleAsn                                           75
GTGGGGGGACATCAAGCAGCCATGCAAATGTTAAAAGAGACCATCAAT                                 240

GluGluAlaGluTrpAspArgValHisProValHisAlaGlyPro                                     91
GAGGAAGCTGAGATGGGATAGAGTGCATCCAGTGCATGCAGGCCT                                   288

IleAlaProGlyGlnMetArgGluProArgGlySerAspIleAlaGly                                 107
ATTGCACCAGGCCAGATGAGAGAACCAAGGGGAAGTGACATAGCAGGA                                 336
```

```
ThrThrSerThrLeuGlnGluGlnIleGlyTrpMetThrAsnAsnPro          123
ACTACTAGTACCCTTCAGGAACAAATAGGATGACAAATAATCCA              384

ProIleProValGlyGluIleTrpLysArgTrpIleIleLeuGlyLeu          139
CCTATCCCAGTAGGAGAAATTTATAAAGATGGATAATCCTGGATTA            432

AsnLysIleValArgMetTyrSerProThrSerIleLeuAspIleArg          155
AATAAGATAGTAAGAATGTATAGCCCTACCAGCATTCTGGACATAAGA          480

GlnGlyProLysGluProPheArgAspTyrValAspArgPheTyrLys          171
CAAGGACCAAAAGGAACCCTTTAGAGACTATGTAGACCGGTTCTATAAA         528

ThrLeuArgAlaGluGlnAlaSerGlnGluValLysAsnTrpMetThr          187
ACTCTAAGAGCCGAGCAAGCTTCACAGGAGGTAAAAAATTGGATGACA          576

GluThrLeuLeuValGlnAsnAlaAsnProAspCysLysThrIleLeu          203
GAAACCTTGTTGGTCCAAAATGCGAACCCAGATTGTAAGACTATTTTA          624

LysAlaLeuGlyProAlaAlaThrLeuGluMetMetThrAlaCys             219
AAAGCATTGGGACCAGCGGCTACACTAGAAGAAATGATGACAGCATGT          672
```

FIG. 1D-2

```
GlnGlyValGlyGlyProAspGlnGlnLeuLeuGlyIleTrpGlyCys                    235
CAGGGAGTAGGAGGACCAGACCAGAGCAGCTGCTGGGTATCTGGGGCTGT                 720

SerGlyLysLeuIleCysThrThrAlaValProTrpAsnGlyProAsp                   251
TCTGGCAAGCTGATCTGTACTACTGCTGTTCCGTGGAACGGACCAGAC                   768

GlnAlaArgLeuAsnSerTrpGlyCysAlaPheArgGlnValGlyHis                   267
CAGGCTCGTCTGAACTCCTGGGGTTGCGCTTTCCGTCAGGTTGGCCAC                   816

ThrThrValProTrpValAsnGlyProAspGlnGlnLeuLeuGlyIle                   283
ACCACCGTTCCGTGGGTTAACGGTCCTGACCAGCAGCTGCTGGGTATC                   864

TrpGlyCysSerGlyLysLeuIleCysThrThrAlaValProTrpAsn                   299
TGGGGCTGTTCTGGCAAGCTGATCTGTACTACTGCTGTTCCGTGGAAC                   912

GlyProAspGlnGlnLeuLeuGlyIleTrpGlyCysSerGlyLysLeu                   315
GGACCAGACCAGCAGCTGCTGGGTATCTGGGGCTGTTCTGGCAAGCTG                   960

IleCysThrThrAlaValProTrpAsnGlyProAspGlyHisLysAlaArg                331
ATCTGTACTACTGCTGTTCCGTGGAACGGACCCGGCCATAAGGCAAGA                  1008

ValLeu                                                             333
GTTTTGTAATAAG                                                     1021
```

FIG. 1D-3

```
                MetProIleValGlnAsnIleGlnGlyGlnMet                        11
AGGAGGGTTTTTCATATGCCAATCGTGCAGAACATCCAGGGGCAAATG                        48

ValHisGlnAlaIleSerProArgThrLeuAsnAlaTrpValLysVal                        27
GTACATCAGGCCATATCACCTAGAACTTAAATGCATGGGTAAAAGTA                         96

ValGluGluLysAlaPheSerProGluValIleProMetPheSerAla                        43
GTAGAAGAGAAGGCTTTCAGCCCAGAAGTGATACCCATGTTTTCAGCA                        144

LeuSerGluGlyAlaThrProGlnAspLeuAsnThrMetLeuAsnThr                        59
TTATCAGAAGGAGCCACCCCACCAAGATTTAAACACCATGCTAAACACA                       192

ValGlyGlyHisGlnAlaAlaMetGlnMetLeuLysGluThrIleAsn                        75
GTGGGGGGACATCAAGCAGCCATGCAAATGTTAAAAGAGACCATCAAT                        240

GluGluAlaAlaGluTrpAspAspArgValHisProValHisAlaGlyPro                     91
GAGGAAGCTGCAGAATGGGATGATAGAGTGCATCCAGTGCATGCAGGGCCT                     288

IleAlaProGlyGlnMetArgGluProArgGlySerAspIleAlaGly                        107
ATTGCACCAGGCCAGATGAGAGAACCAAGGGGAAGTGACATAGCAGGA                        336
```

FIG. 1E-1

```
ThrThrSerThrLeuGluGlnIleGlyTrpMetThrAsnPro                          123
ACTACTAGTACCCTTCAGGAACAAATAGGATGGATGACAAATAATCCA                    384

ProIleProValGlyGluIleTryLysArgTrpIleIleLeuGlyLeu                    139
CCTATCCCAGTAGGAGAGAATTTATAAAGATGGATAATCCTGGGATTA                    432

AsnLysIleValArgMetTyrSerProThrSerIleLeuAspIleArg                    155
AATAAAATAGTAAGAATGTATAGCCCTACCAGCATTCTGGACATAAGA                    480

GlnGlyProLysGluProPheArgAspTyrValAspArgPheTyrLys                    171
CAAGGACCAAAGGAACCCTTTAGAGACTATGTAGACCGGTTCTATAAA                    528

ThrLeuArgAlaGluGlnAlaSerGlnGluValLysAsnTrpMetThr                    187
ACTCTAAGAGCCGAGCAAGCTTCACAGGAGGTAAAAAATTGGATGACA                    576

GluThrLeuLeuValGlnAsnAlaAsnProAspCysLysThrIleLeu                    203
GAAACCTTGTTGTTCCAAAATGCGAACCCAGATTGTAAGACTATTTTA                    624

LysAlaLeuGlyProAlaAlaThrLeuGluMetMetThrAlaCys                       219
AAAGCATTGGGACCAGCGGCTACACTAGAGAAGAAATGATGACAGCATGT                  672
```

FIG. 1E-2

```
GlnGlyValGlyGlyProAspGlnGlnLeuLeuGlyIleTrpGlyCys          235
CAGGGAGTAGGAGGACCAGACCAGCTGGGTATCTGGGCTGT                 720

SerGlyLysLeuIleCysThrThrAlaValProTrpAsnGlyProAsp          251
TCTGGCAAGCTGATCTGTACTACTGCTGTTCCGTGGAACGGACCAGAC          768

GlnAlaArgLeuAsnSerTrpGlyCysAlaPheArgGlnValCysHis          267
CAGGCTCGTCTGAACTCCTGGGGTTGCGCCTTTCCGTCAGGTTGCCAC          816

ThrThrValProTrpValAsnGlyProGlyHisLysAlaArgValLeu          283
ACCACCGTTCCGTGGGTTAACGGACCCGGCCATAAGGCAAGAGTTTTG          864

TAATAAG                                                   283
                                                          871
```

FIG. IE-3

C-terminus 224 of p24
|
p24: GGPGHKARVL p24/p41: GGPDQQLLGIWGCSGKLICTTAVPWNGPGHKARVL

METHODS AND SYSTEMS FOR PRODUCING HIV ANTIGENS

CROSS REFERENCE TO RELATED APPLICATION

This is a continuation-in-part application of copending applications Ser. No. 191,229, filed May 6, 1988, Ser. No. 206,499, filed Jun. 13, 1988, and Ser. No. 258,016, filed Oct. 14, 1988, all abandoned, the disclosures of each of which are hereby incorporated by reference.

TECHNICAL FIELD

The present invention relates to a segment of deoxyribonucleic acid (DNA) that encodes either a recombinant HIV p24 protein and/or a HIV p24-gp41 fusion protein and a recombinant DNA (rDNA) that contains the DNA segment. Cells transformed with a rDNA of the present invention and methods for producing HIV p24-gp41 fusion protein are also contemplated.

BACKGROUND OF THE INVENTION

The human immunodeficiency virus, (HIV), is believed to be the causative agent of Acquired Immunodeficiency Syndrome (AIDS). The nucleic acid sequence of the HIV proviral genome has been deduced and the location of various protein coding regions within the viral genome has been determined.

Of particular interest to the present invention is that portion of the HIV genome known in the art as the gag region. The gag region is believed to encode a precursor protein that is cleaved and processed into three mature proteins, p17, p24 and p15. The HIV p24 protein has an apparent relative molecular weight of about 24,000 daltons and is known in the art as the HIV core antigen because it forms the viral capsid.

The p24 antigen of HIV is of particular interest because studies have indicated that the first evidence of anti-HIV antibody formation (sero- conversion) in infected individuals is the appearance of antibodies induced by the p24 antigen, i.e., anti-p24 antibodies. In addition, recent studies have reported that p24 protein can be detected in blood samples even before the detection of anti p24 antibodies. Detecting the presence of either the p24 protein or anti-p24 antibodies therefore appear to be the best approach to detecting HIV infection at the earliest point in time.

Furthermore, the p24 antigen reappears in the blood of infected individuals concomitant with the decline of anti-p24 antibody in patients showing the deterioration in their clinical condition that accompanies transition into full-blown AIDS. Thus, the p24 antigen can serve as an effective prognostic marker in patients undergoing therapy.

The development of immunoassays for detecting anti-p24 antibodies has been limited by difficulties in producing sufficient quantities of HIV p24 protein that is essentially free of immunoreactive contaminants. The presence of contaminants that immunoreact with antibodies present in patient samples results in lower assay specificity and sensitivity and an increase in false positive results.

Presently, when assaying for anti-p24 antibodies in a blood sample, the art typically overcomes the presence of contaminants in HIV p24 protein preparations by preabsorbing the sample with a preparation containing the contaminants. For instance, Dowbenko et al., *Proc Natl Acad Sci USA* 82: 7748-7752 (1985) reported using recombinant DNA methods to produce in *E. coli* a HIV p24 fusion protein. However, an immunoaffinity-purified preparation of the p24 fusion protein contained a level of *E. coli* protein contaminants sufficient to require preabsorbing the blood samples being tested with *E. coli* protein extracts.

Similarly, Steimer et al., *Virol.*, 150: 283-290 (1986) reported producing a truncated HIV p24 in *E. coli*. The truncated p24 was isolated from contaminating *E. coli* proteins using ammonium sulfate precipitation and fractionation by gel filtration to produce a p24 antigen preparation described as being greater than 99% pure. However, use of that p24 antigen preparation in an enzyme linked immunosorbent assay (ELISA) to detect anti-p24 antibodies still required preabsorbing the blood samples with *E. coli* proteins. European patent application No. 85309454.8, published Jul. 9, 1986 (publication No. 0187041) also describes the expression of HIV p24 fusion protein in *E. coli*.

Two difficulties in using genetically engineered *E. coli* to produce a HIV p24 antigen preparation that is essentially free of contaminating *E. coli* proteins are insolubility and low yield of the recombinantly produced protein. For example, Dowbenko et al., supra, Ghrayeb et al., *DNA*, 5: 93-99 (1986) and Shoeman et al., *Anal. Biochem.*, 161: 370-379 (1987) have reported that HIV p24 fusion proteins produced in *E. coli* accumulated as insoluble aggregates ("inclusion bodies") within the producing bacteria. The aggregates, which can be seen as granules in electron micrographs of the bacteria, were recovered in the pellet fraction after cell lysis (breakage) and centrifugation. Solubilization of the protein from the pellet then required treatment with strong denaturing agents.

The yield of a recombinant protein from transformed bacteria is directly related to its translation rate. A recombinant protein cannot be synthesized faster than the slowest step in the entire translation process. Translation initiation, elongation and termination have all been found to be steps whose efficiency is not predictable from DNA sequence alone.

For example, Steimer et al., supra, reported examining the effect on translation efficiency of varying the three nucleotides 5' of the initiator AUG in a rDNA coding for an amino-terminal truncated HIV p24 protein. This area of the rDNA was examined because it is involved in defining the translation initiation (ribosome binding) site. Steimer et al. found that the efficiency of translation initiation depended upon the integration of several factors and was not predictable from the DNA sequence of the ribosome binding site region.

SUMMARY OF THE INVENTION

The present invention contemplates a DNA segment comprising a first nucleotide base sequence operatively linked at its 3' terminus to the 5' terminus of a second nucleotide base sequence. The first sequence has a nucleotide base sequence represented by the formula:

AGGAGGGTTTTTCAT.

The second sequence has a nucleotide base sequence that codes for a recombinant HIV p24 protein.

The present invention also contemplates a recombinant DNA comprising a vector operatively linked to a DNA segment. The DNA segment comprises a first nucleotide base sequence operatively linked at its 3' terminus to the 5' terminus of a second nucleotide base sequence. The first sequence has a nucleotide base sequence represented by the formula:

AGGAGGGTTTTTCAT.

The second sequence has a nucleotide base sequence that codes for a recombinant HIV p24 protein.

The present invention contemplates a DNA segment encoding an amino acid residue sequence represented by FIG. 1B from residue 1 to about residue 257, by FIG. 1C from residue 1 to residue 258 or by FIG. 1E from residue 1 to residue 283. Preferably the DNA segment has a particular nucleotide base sequence represented by FIG. 1B, 1C or 1E.

Also contemplated is a recombinant DNA molecule comprising a vector, preferably an expression vector, operatively linked to a DNA segment of the present invention. A preferred recombinant DNA molecule is pGEXp24gp41, pGEXp24gp41-2 or pGEXp24gp41-1,2.

A HIV p24-gp41 fusion protein having an amino acid residue sequence represented by FIG. 1B from residue 1 or 2 to about residue 257, by FIG. 1C from residue 1 or 2 to about residue 258 or by FIG. 1E from residue 1 or 2 to about residue 283 is also contemplated.

Further contemplated is a culture of cells transformed with a recombinant DNA molecule of this invention and methods of producing the recombinant HIV p24 or HIV p24-gp41 fusion proteins of this invention using the culture.

Also contemplated is a composition comprising recombinant HIV p24 protein. The composition is further characterized as being essentially free of (a) procaryotic antigens, and (b) other HIV-related proteins.

Still further contemplated is a diagnostic system in kit form comprising, in an amount sufficient to perform at least one assay, a recombinant HIV p24 protein composition of this invention, as a separately packaged reagent.

In another embodiment, the present invention contemplates a diagnostic system, in kit form, comprising a HIV p24-gp41 fusion protein of this invention. Preferably, the diagnostic system contains the HIV p24-gp41 fusion protein affixed to a solid matrix.

Further contemplated is a method of assaying a body fluid sample for the presence of antibodies against at least one of the HIV antigens p24 and gp41. The method comprises forming an immunoreaction admixture by admixing the body fluid sample with a HIV p24-gp41 fusion protein of this invention. The immunoreaction admixture is maintained for a time period sufficient for any of the antibodies present to immunoreact with the fusion protein to form an immunoreaction product, which product, when detected, is indicative of the presence of anti-HIV p24 and/or anti-HIV gp41 antibodies. Preferably, the fusion protein is affixed to a solid matrix when practicing the method.

In another embodiment, this invention contemplates an inoculum comprising a therapeutically effective amount of recombinant HIV p24 protein in a pharmaceutically acceptable carrier. The inoculum is essentially free of (a) procaryotic antigens, and (b) other HIV-related proteins.

A method for treating HIV infection, which method comprises administering an inoculum of the present invention, is also contemplated.

Figures 1, 2A:
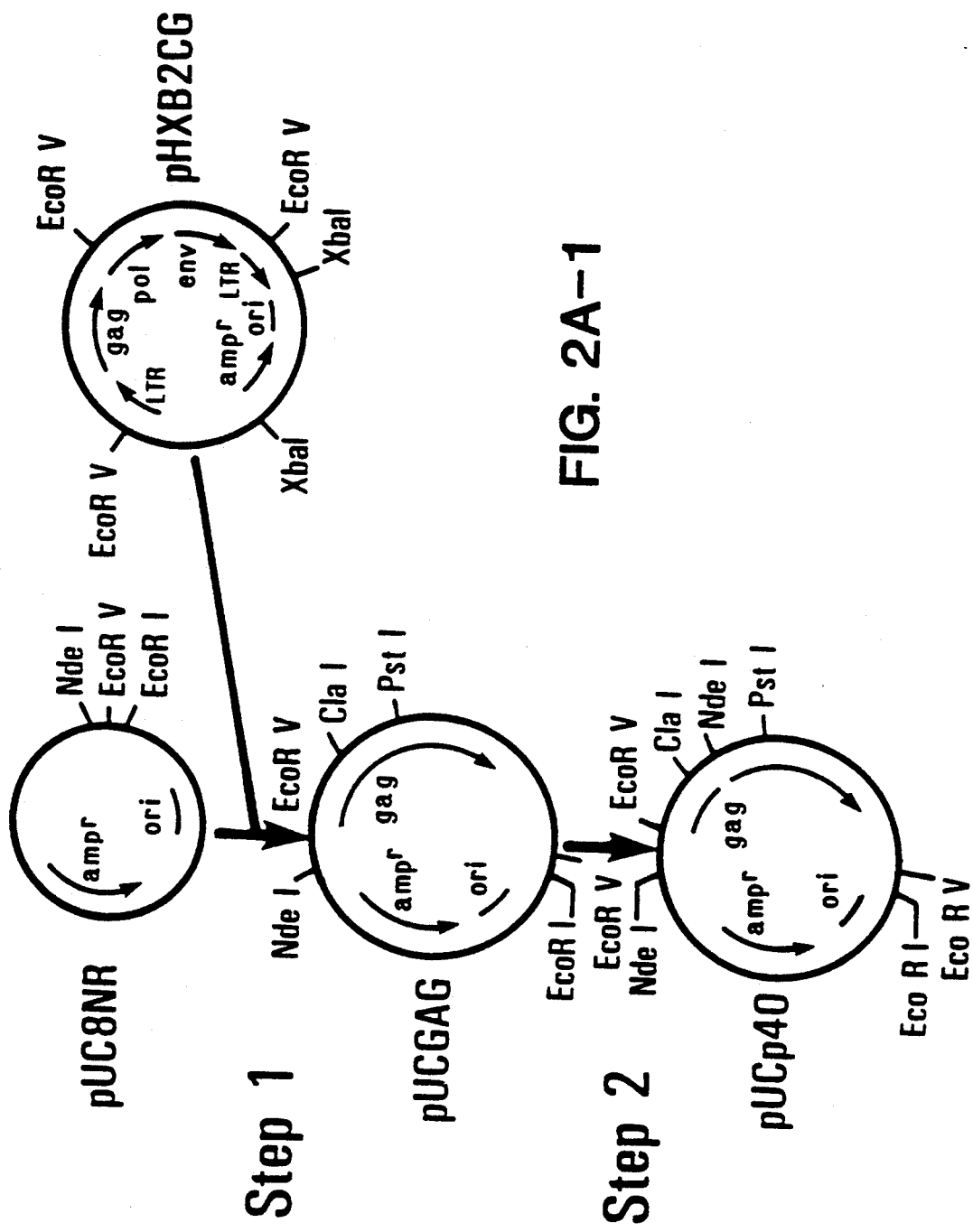
FIG. 1, containing panels 1A-1, 1A-2, 1B-1, 1B-2, 1B-3, 1C-1, 1C-2, 1C-3, 1D-1, 1D-2, 1D-3, 1E-1, 1E-2, and 1E-3, illustrates the nucleotide base sequences of preferred DNA segments of the present invention. The base sequences are shown conventionally from left to right and in the direction of 5' terminus to 3' terminus using the single letter nucleotide base code (A=adenine, T=thymine, C=cytosine and G=guanine). In all panels of FIG. 1 nucleotide bases 1-4 represent the Shine-Dalgarno sequence [Shine et al., Proc. Natl. Acad. Sci. USA, 71:1342 (1974)] bases 1-15 define a ribosome binding site; and bases 16-690 define a majority of the recombinant HIV p24 protein structural gene.

The reading frame of the structural genes illustrated in all panels of FIG. 1 is indicated by placement of the deduced amino acid residue sequence of the protein for which it codes above the nucleotide sequence such that the triple letter code for each amino acid residue (Table of Correspondence) is located directly above the three bases (codon) coding for each residue. The residue sequence is shown conventionally from left to right and in the direction of amino terminus to carboxy terminus. The position in the respective amino acid residue and nucleotide base sequences of the right-hand most residue and base is indicated by the numbers in the right margin of the figure. The DNA encoded amino acid residue sequence of preferred recombinant HIV-related proteins are shown above the structural gene that encodes each protein.

The nucleotide base sequences represented by bases 15-718, 15-793, 15-796, 15-1021 and 15-821, in panels 1A, 1B, 1C, 1D and 1E respectively, illustrate preferred DNA segments, each having a 5' coding strand terminus complementary to a nucleotide base sequence produced by cleavage with the restriction endonuclease Nde I, i.e., a Nde I cohesive terminus, and a 3' coding strand terminus complementary to a nucleotide base sequence produced by cleavage with the restriction endonuclease BamH I, i.e., a BamH I cohesive terminus.

The recombinant HIV p24 protein illustrated in panel 1A contains an amino acid residue sequence corresponding to residues 1-232.

The HIV p24-gp41 fusion protein (p24-A5) illustrated in panel 1B contains an amino-terminal HIV p24 polypeptide portion corresponding to residues 1-225, an intermediate HIV gp41 polypeptide portion corresponding to residues 226-248, a Gly-Pro dipeptide linker portion corresponding to residues 249-250, and a carboxy-terminal HIV p24 polypeptide portion corresponding to residues 251-257.

The HIV p24-gp41-2 fusion protein (p24-A2) illustrated in panel 1C contains an amino-terminal HIV p24 polypeptide portion corresponding to residues 1-225, an intermediate HIV gp41 polypeptide portion corresponding to residues 226-249, a Gly-Pro dipeptide linker portion corresponding to residues 250-251, and a carboxy-terminal HIV p24 polypeptide portion corresponding to residues 252-258.

The HIV p24-gp41-1,2,1,1 fusion protein (p24-A5-A2-A5-A5) illustrated in panel 1D contains an amino-terminal HIV p24 polypeptide portion corresponding to residues 1-225, four intermediate HIV gp41 polypeptide portions corresponding to to residues 226-248, 251-274, 277-299, and 302-324, four Gly-Pro dipeptide linker portions corresponding to residues 249-250, 275-276, 300-301 and 325-326, and a carboxy-terminal HIV p24 polypeptide portion corresponding to residues 327-333.

The HIV p24-gp41-1,2 fusion protein (p24-A5-A2) illustrateted in panel 1E contains an amino-terminal HIV p24 polypeptide portion corresponding to residues 1-225, two intermediate HIV gp41 polypeptide portions corresponding to residues 226-248 and 251-274, two Gly-Pro dipeptide linker portions corresponding to residues 249-250 and 275-276, and a carboxy-terminal HIV p24 polypeptide portion corresponding to residues 277-283.

Figures 2, 2A:
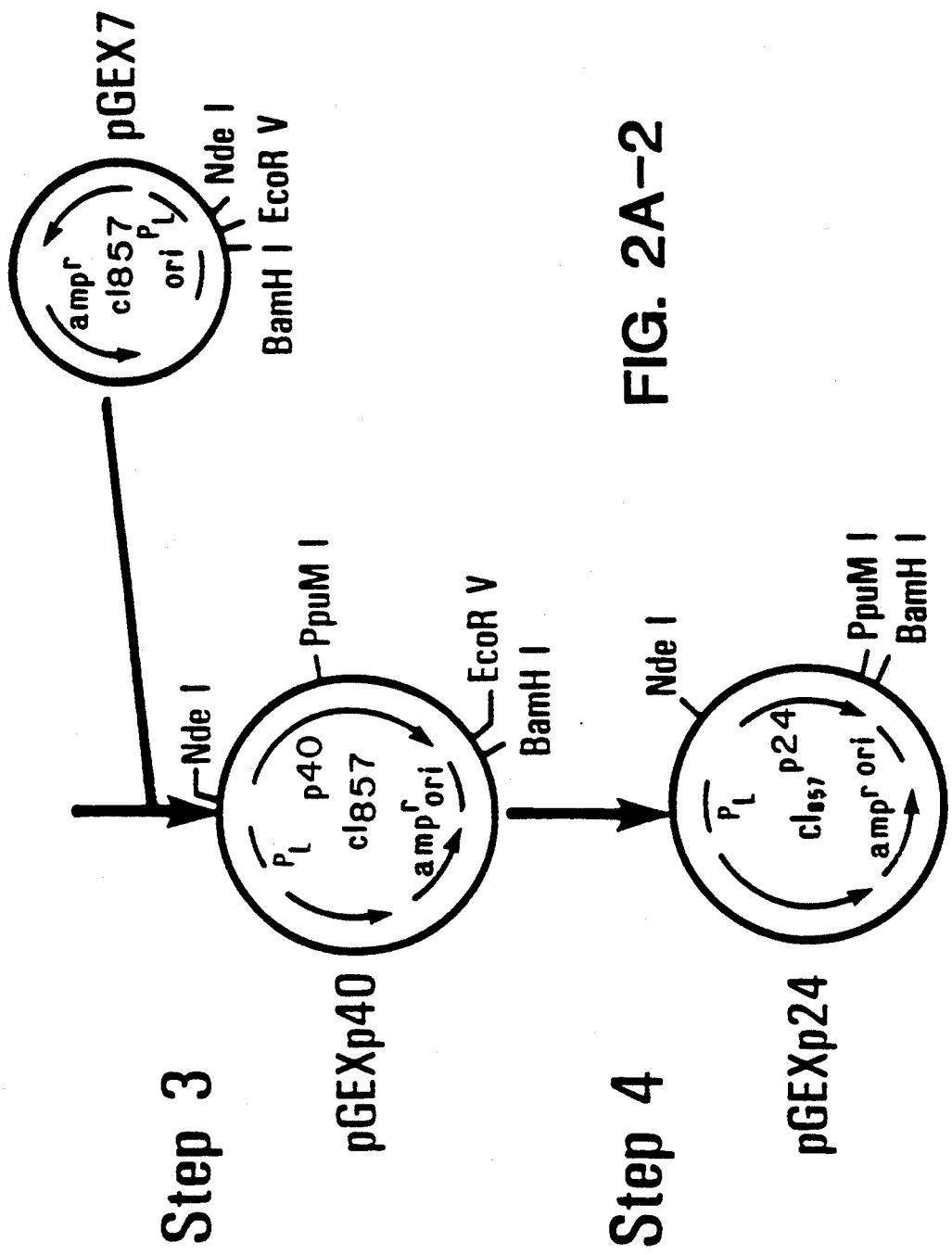

FIG. 2, panels 2A-1 and 2A-2 illustrates construction of the pGEXp24 recombinant DNA for expressing recombinant HIV p24 protein in *E. coli*. The recombinant DNAs manipulated and produced by the construction process are indicated in the figure by the circles. The construction proceeds by a series of steps as indicated by the arrows connecting the circles in the figure and as described in detail in Example 1. Landmark and utilized restriction enzyme recognition sites are indicated on the circles by labeled lines intersecting the circles. The relative location of individual genes and their direction of transcription are indicated by the labeled arrows inside the circles.

Panel B of FIG. 2 illustrates construction of the recombinant DNA plasmid pGEXp24gp41 by ligating an oligonucleotide coding for the single underlined amino acid residue sequence (peptide A5) into the PpuM I restriction site located within the HIV p24 structural gene of pGEXp24. The ligation resulted in the formation of a structural gene, shown in FIG. 1B, operatively linked to the pGEX7 vector and coding for the HIV p24-gp41 fusion protein also shown in FIG. 1B (residues 1-257).

Figure 3:
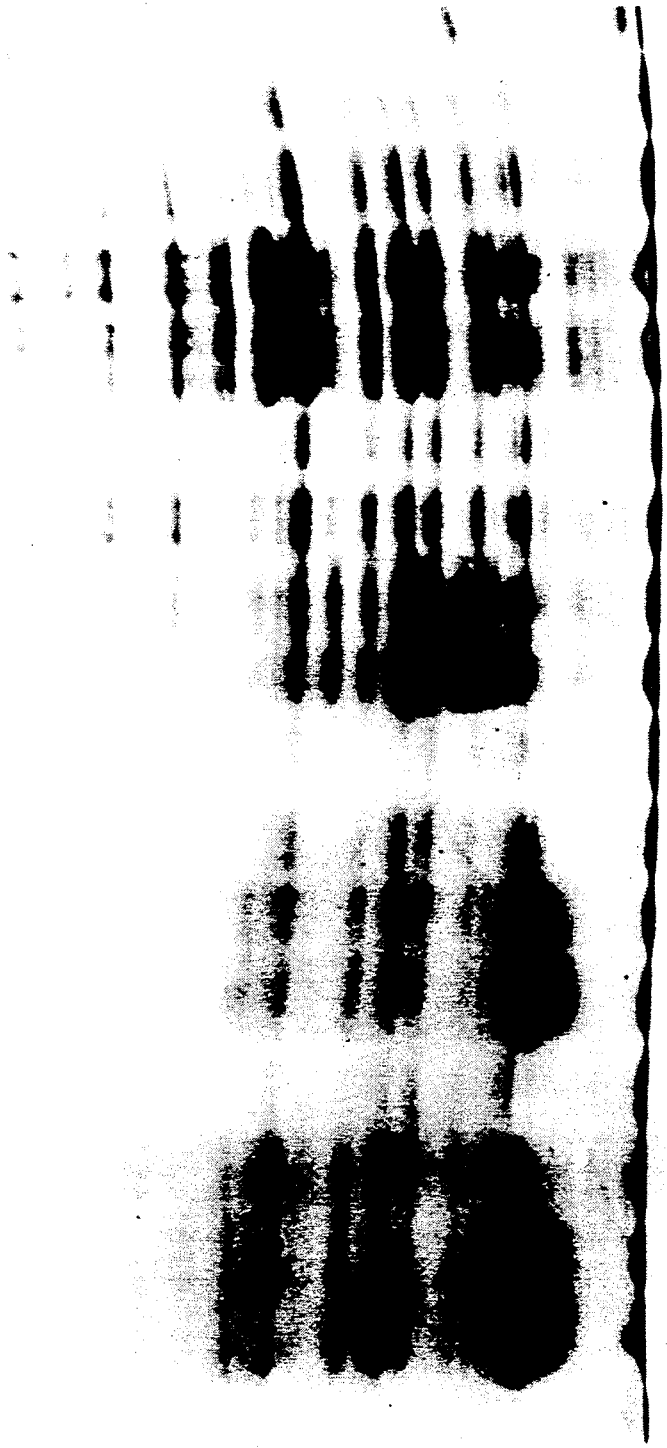

FIG. 3 illustrates SDS-PAGE of bacterial cell lysates containing the pGEXp24 plasmid. Cells were held at 42 degrees C (42° C.) for 0 minutes (lane 1), 0.5 hours (lane 2), 1 hour (lane 3) and 2 hours (lane 4).

Figure 4:
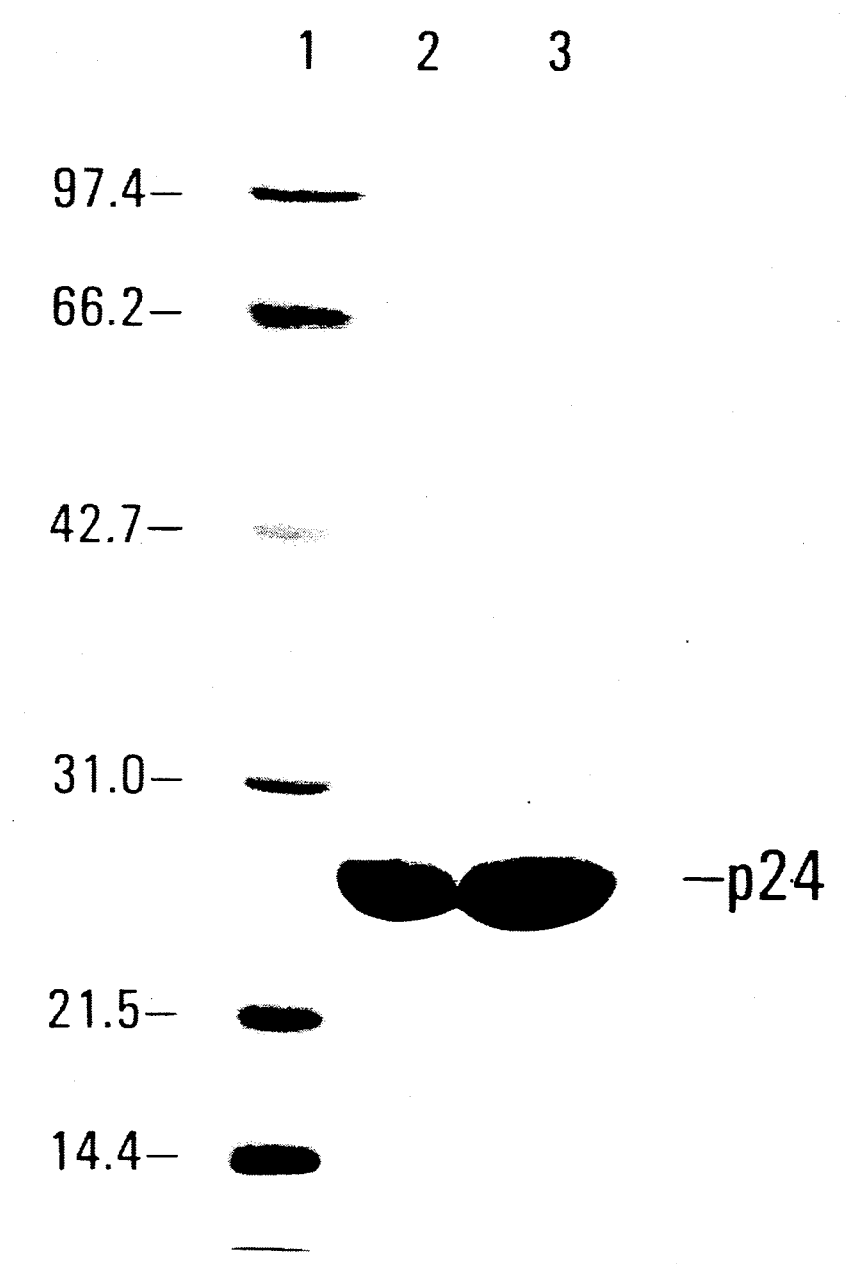

FIG. 4 illustrates SDS gel electrophoresis of purified recombinant p24 polypeptide from HIV-1 gag. Lane A contains the low molecular weight standards, shown in kilodaltons in the left margin, (catalog No. 161,030; Biorad, Richmond, Calif.). Lanes B and C contain 12 and 24 micrograms, respectively, of essentially pure recombinant HIV p24 protein of the invention.

Figure 5:
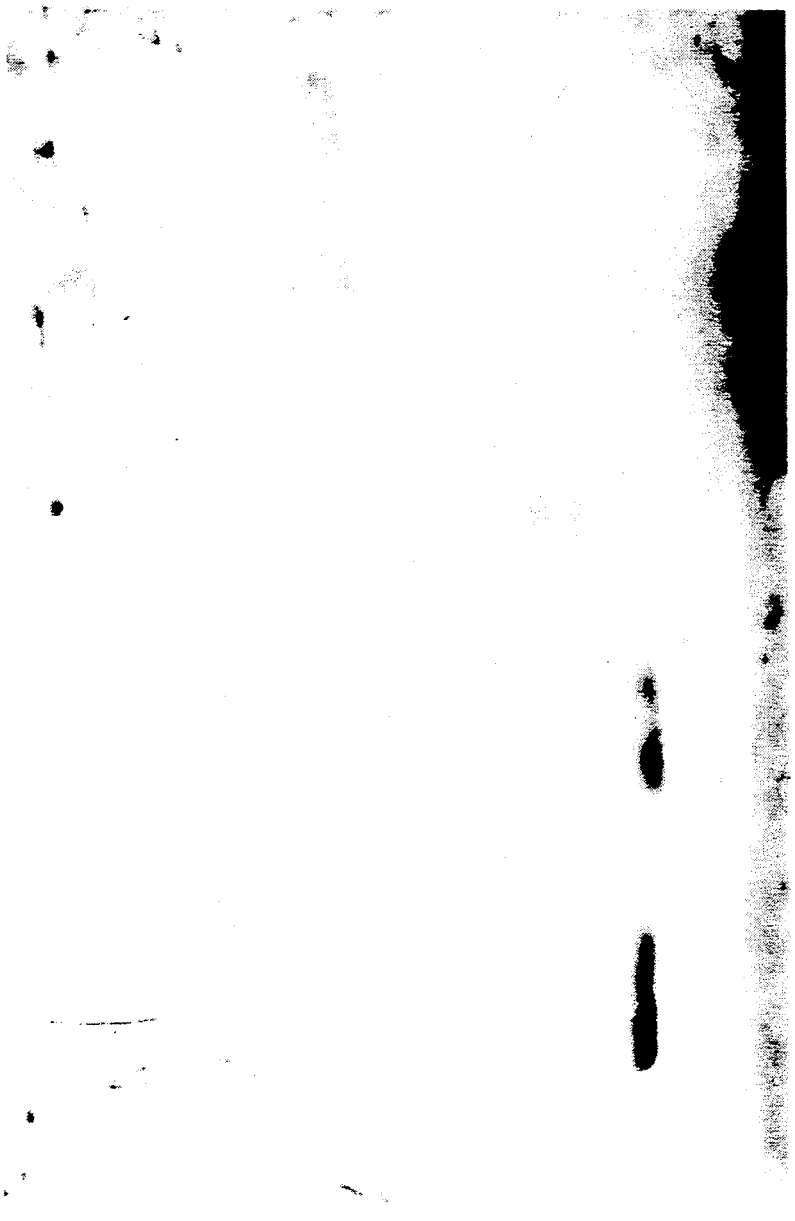

FIG. 5 illustrates a Western blot, prepared as described in Example 3E, using a SDS-PAGE gel of *E. coli* transformed with pGEXp24 plasmid. After induction at 42° C., cell lysates were prepared at 0 minutes (lane 1), 30 minutes (lane 2), 1 hour (lane 3) and 2 hours (lane 4).

FIG. 6 illustrates the carboxy termini of the recombinant HIV p24 protein and HIV p24-gp41 fusion proteins of the present invention. The upper portion of the Figure depicts the amino acid residue sequence from the amino- to carboxy-terminus and in the direction from left to right, of the polypeptides A5 and A2. The lower portion depicts the amino acid residue sequence of the carboxy termini of five HIV antigens of the present invention: recombinant HIV p24 protein (p24), and the HIV fusions proteins p24gp41, p24gp41-2, p24gp41-1,2 and p24gp41-1,2,1,1.

DETAILED DESCRIPTION OF THE INVENTION

A. Definitions

Amino Acid: All amino acid residues identified herein are in the natural L-configuration. In keeping with standard polypeptide nomenclature, *J. Biol. Chem.*, 243:3557-59, (1969), abbreviations for amino acid residues are as shown in the following Table of Correspondence:

| TABLE OF CORRESPONDENCE | | |
|---|---|---|
| SYMBOL | | |
| 1-Letter | 3-Letter | AMINO ACID |
| Y | Tyr | L-tyrosine |
| G | Gly | glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-asparagine |
| C | Cys | L-cysteine |

It should be noted that all amino acid residue sequences, typically referred to herein as "residue sequences", are represented herein by formulae whose left to right orientation is in the conventional direction of amino-terminus to carboxy-terminus.

Nucleotide: a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose it is referred to as a nucleotide. A sequence of operatively linked nucleotides is typically referred to herein as a "base sequence", and is represented herein by a formula whose left to right orientation is in the conventional direction of 5'-terminus to 3'-terminus.

Base Pair (bp): A partnership of adenine (A) with thymine (T), or of cytosine (C) with guanine (G) in a double stranded DNA molecule.

B. DNA Segments

In living organisms, the amino acid residue sequence of a protein or polypeptide is directly related via the genetic code to the deoxyribonucleic acid (DNA) sequence of the structural gene that codes for the protein. Thus, a structural gene can be defined in terms of the amino acid residue sequence, i.e., protein or polypeptide, for which it codes.

An important and well known feature of the genetic code is its redundancy. That is, for most of the amino acids used to make proteins, more than one coding nucleotide triplet (codon) can code for or designate a particular amino acid residue. Therefore, a number of different nucleotide sequences may code for a particular amino acid residue sequence. Such nucleotide sequences are considered functionally equivalent since they can result in the production of the same amino acid residue sequence in all organisms. Occasionally, a methylated variant of a purine or pyrimidine may be incorporated into a given nucleotide sequence. However, such methylations do not affect the coding relationship in any way.

In one embodiment, a DNA segment of the present invention comprises a first nucleotide base sequence that defines a ribosome binding site and has a sequence represented by the formula:

AGGAGGGTTTTTCAT.

The first sequence is operatively linked at its 3' terminus to the 5' terminus of a second nucleotide base sequence that defines a structural gene capable of expressing a recombinant HIV p24 protein. A preferred DNA segment has a base sequence represented by the base sequence shown in FIG. 1A from base position 1 to base position 711 or 718. Preferred DNA segments further include the base sequence TAATAA (a base sequence representing two adjacent stop signals) operatively linked to the 3'-terminus of the structural gene. In preferred embodiments, the length of the first and second nucleotide base sequences, when linked, is no more than about 711 bases, and more preferably no more than about 10,000 bases. In addition, a DNA segment of this invention does not code for any other protein, or antigenically identifiable portion thereof, coded for by the gag region of the HIV genome.

As used herein, the phrase "recombinant HIV p24 protein" refers to a protein of about 231 amino acid residues in length that has an amino acid residue sequence homologous to a naturally occurring mature HIV p24 protein. The nucleotide base residues 16–18 encode terminal methionine residue, shown in all panels of FIG. 1, to facilitate initiation of protein translation at an ATG codon, as is well known. However, in the bulk of the expressed protein, the methionine is cleaved off during protein translation and processing to produce a protein that begins at amino acid residue 2 (Proline). A recombinant HIV p24 protein is further characterized as being water soluble and as not expressing any HIV p17 or p15 antigenic determinants. The amino acid residue sequence of a preferred recombinant HIV p24 protein is shown in FIG. 1A from residue 2 to residue 232.

In another embodiment, a DNA segment of this invention contains a nucleotide base sequence that defines a structural gene capable of expressing a HIV p24-gp41 fusion protein. The phrase "HIV p24-gp41 fusion protein" refers to a protein having an amino-terminal HIV p24 polypeptide portion operatively linked by a peptide bond at its carboxy-terminus to a HIV gp41 polypeptide portion. The HIV p24 polypeptide portion has an amino acid residue sequence corresponding to a sequence as shown in FIG. 1B from about residue 2 to about residue 225. HIV p24-gp41 fusion protein in its expressed form has an amino acid residue sequence that begins at residue 2 (Proline), having the amino terminal methionine residue cleaved off during protein translation and processing as above for expressed HIV p24 protein. The HIV gp41 polypeptide portion has an amino acid residue sequence corresponding to a polypeptide capable of immunoreacting with anti-HIV gp41 antibodies, i.e., a polypeptide displaying HIV gp41 antigenicity (an HIV gp41-antigenic polypeptide). Polypeptides displaying HIV gp41 antigenicity are well known in the art. See, for example, the U.S. Pat. No. 4,629,783 to Cosand, U.S. Pat. No. 4,735,896 to Wang et al., and Kennedy et al., *Science,* 231:1556–1559 (1986).

A preferred HIV gp41 polypeptide portion of a HIV p24-gp41 fusion protein has an amino acid residue sequence represented by the sequence shown in FIG. 1B from residue 226 to residue 248 or by the sequence shown in FIG. 1C from residue 226 to residue 249.

In one embodiment, a HIV p24-gp41 fusion protein contains more than one HIV gp41 polypeptide portion, as for example the combination of two different HIV gp41 polypeptide portions represented by the sequence shown in FIG. 1D from residue 226 to residue 324, or in FIG. 1E from residue 226 to residue 274.

In preferred embodiments, the HIV gp41 polypeptide portion of a HIV p24-gp41 fusion protein of this invention contains at least 10 amino acid residues, but no more than about 35 amino acid residues, and preferably has a length of about 15 to about 25 residues.

In preferred embodiments, that portion of a HIV p24-gp41 fusion protein encoding DNA segment of this invention that codes for the HIV p24 polypeptide portion has a nucleotide base sequence corresponding to a sequence that codes for an amino acid residue sequence as shown in FIG. 1B from about residue 1 to about residue 225, and more preferably has a nucleotide base sequence corresponding to a base sequence as shown in FIG. 1B from base 16 to base 690.

In preferred embodiments, that portion of a HIV p24-gp41 fusion protein encoding DNA segment of this invention that codes for the HIV gp41 polypeptide portion has a nucleotide base sequence corresponding to a sequence that codes for an amino acid residue sequence as shown in FIG. 1B from residue 226 to residue 248, in FIG. 1C from residue 226 to residue 249, in FIG. 1D from residue 226 to residue 324, or in FIG. 1E from residue 226 to residue 274. More preferably that portion of the DNA segment coding for the HIV gp41 polypeptide portion has a nucleotide base segment corresponding in base sequence to the sequence shown in FIG. 1B from base 691 to base 759, in FIG. 1C from base 691 to base 762, in FIG. 1D from base 691 to base 987, or in FIG. 1E from base 691 to base 837.

Most preferably, a HIV p24-gp41 fusion protein encoding DNA segment of this invention has a nucleotide base sequence corresponding to the sequence shown in (1) FIG. 1B from base 1 to base 786, base 15 to base 786, base 16 to base 786, base 1 to base 793, base 15 to base 793, or base 16 to base 793; in (2) FIG. 1C from base 1 to base 789, base 15 to base 789, base 16 to base 789, base 1 to base 796, base 15 to base 796, or base 16 to base 796; in (3) FIG. 1D from base 1 to base 1014, base 15 to base 1014, base 16 to base 1014, base 1 to base 1021, base 15 to base 1021, or base 16 to base 1021; or in (4) FIG. 1E from base 1 to base 864, base 15 to base 864, base 16 to base 864, base 1 to base 871, base 15 to base 871, or base 16 to base 871.

In preferred embodiments, a DNA segment of the present invention is bound to a complimentary DNA segment, thereby forming a double stranded DNA segment. Preferably, a double stranded DNA segment of this invention includes no more than about 800 base pairs, preferably no more than about 5000 base pairs, and more preferably no more than about 10,000 base pairs. In addition, it should be noted that a double stranded DNA segment of this invention preferably has a single stranded cohesive tail at one or both of its termini.

A DNA segment of the present invention can easily be prepared from isolated virus obtain from HIV-infected individuals or synthesized by chemical techniques, for example, the phosphotriester method of Matteucci et al., J. Am. Chem. Soc., 103:3185 (1981). (The disclosures of the art cited herein are incorporated herein by reference.) Of course, by chemically synthesizing the structural gene portion, any desired modifications can be made simply by substituting the appropriate bases for those encoding a native amino acid residue. However, DNA segments including sequences identical to a segment shown in FIGS. 1A, 1B, 1C, 1D or 1E are preferred.

C. Recombinant DNA Molecules

Figure 2B:
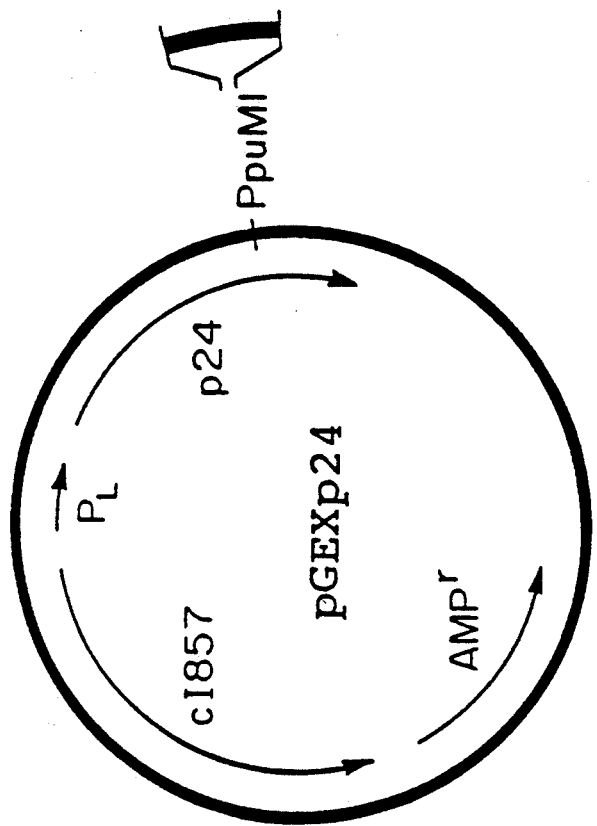

The present invention further contemplates a recombinant DNA (rDNA) that includes a DNA segment of the present invention operatively linked to a vector. A preferred rDNA of the present invention is characterized as being capable of directly expressing, in a compatible host, recombinant HIV p24 protein or HIV p24-gp41 fusion protein. By "directly expressing" is meant that the mature polypeptide chain of the protein is formed by translation alone as opposed to proteolytic cleavage of two or more terminal amino acid residues from a larger translated precursor protein. Preferred rDNAs of the present invention are the rDNA plasmids pGEXp24 and pGEXp24gp41 illustrated in FIGS. 2A and 2B, respectively, and the rDNA plasmids pGEXp24gp41-2 and pGEXp24gp41-1,2 described in Example 1B.

A recombinant DNA molecule of the present invention can be produced by operatively linking a vector to a DNA segment of the present invention.

As used herein, the term "vector" refers to a DNA molecule capable of autonomous replication in a cell and to which another DNA segment can be operatively linked so as to bring about replication of the attached segment. Vectors capable of directing the expression of a HIV p24 protein or HIV p24-gp41 fusion protein structural gene are referred to herein as "expression vectors". Thus, a recombinant DNA molecule (rDNA) is a hybrid DNA molecule comprising at least two nucleotide sequences not normally found together in nature.

The choice of vector to which a DNA segment of the present invention is operatively linked depends directly, as is well known in the art, on the functional properties desired, e.g., protein expression, and the host cell to be transformed, these being limitations inherent in the art of constructing recombinant DNA molecules. However, a vector contemplated by the present invention is at least capable of directing the replication, and preferably also expression, of the recombinant HIV p24 or HIV p24-gp41 fusion protein structural gene included in DNA segments to which it is operatively linked.

In preferred embodiments, a vector contemplated by the present invention includes a procaryotic replicon (ori), i.e., a DNA sequence having the ability to direct autonomous replication and maintenance of the recombinant DNA molecule extrachromosomally in a procaryotic host cell, such as a bacterial host cell, transformed therewith. Such replicons are well known in the art. In addition, those embodiments that include a procaryotic replicon also typically include a gene whose expression confers drug resistance to a bacterial host transformed therewith. Typical bacterial drug resistance genes are those that confer resistance to ampicillin or tetracycline.

Those vectors that include a procaryotic replicon can also include a procaryotic promoter capable of directing the expression (transcription and translation) of the recombinant HIV p24 structural gene or HIV p24-gp41 fusion protein structural gene in a bacterial host cell, such as $E.$ $coli$, transformed therewith. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Typical of such vector plasmids are pUC8, pUC9, pBR322 and pBR329 available from Biorad Laboratories, (Richmond, Calif.) and pPL and pKK223 available from Pharmacia, Piscataway, N.J.

A variety of methods have been developed to operatively link DNA segments to vectors via complementary cohesive termini. For instance, complementary homopolymer tracts can be added to the DNA segment to be inserted and to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, generated by endonuclease restriction digestion as described earlier, is treated with bacteriophage T4 DNA polymerase or $E.$ $coli$ DNA polymerase I, enzymes that remove protruding, 3', single-stranded termini with their 3'–5' exonucleolytic activities and fill in recessed 3' ends with their polymerizing activities. The combination of these activities therefore generates blunt-ended DNA segments The blunt-ended segments are then incubated with a large molar excess of linker molecules in the presence of an enzyme that is able to catalyze the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease sites are commercially available from a number of sources including International Biotechnologies, Inc., New Haven, Conn.

Also contemplated by the present invention are RNA equivalents of the above described recombinant DNA molecules.

D. Transformed Cells and Cultures

The present invention also relates to a procaryotic host cell transformed with a recombinant DNA molecule of the present invention, preferably an rDNA capable of expressing a recombinant HIV p24 or HIV p24-gp41 fusion protein, and more preferably rDNA plasmid pGEXp24, pGEXp24gp41, pGEXp24gp41-2 or pGEXp24gp41-1,2. Bacterial cells are preferred procaryotic host cells and typically are a strain of $E.$ $coli$, such as, for example, the $E.$ $coli$ strain DH5 available from Bethesda Research Laboratories, Inc., Bethesda, Md. Transformation of appropriate cell hosts with a recombinant DNA molecule of the present invention is accomplished by well known methods that typically depend on the type of vector used. With regard to transformation of procaryotic host cells, see, for example, Cohen et al., *Proc. Natl. Acad. Sci. USA*, 69:2110 (1972); and Maniatis et al., *Molecular Cloning, A Laboratory*

*Mammal*, Cold Spring Harbor Laboratory, Cold Spring Harbor, N.Y. (1982).

Successfully transformed cells, i.e., cells that contain a recombinant DNA molecule of the present invention, can be identified by well known techniques. For example, cells resulting from the introduction of an rDNA of the present invention can be cloned to produce monoclonal colonies. Cells from those colonies can be harvested, lysed and their DNA content examined for the presence of the rDNA using a method such as that described by Southern, *J. Mol. Biol.*, 98:503 (1975) or Berent et al., *Biotech.*, 3:208 (1985).

In addition to directly assaying for the presence of rDNA, successful transformation can be confirmed by well known immunological methods when the rDNA is capable of directing the expression of HIV p24. For example, cells successfully transformed with an expression vector produce proteins displaying HIV core (p24) antigenicity. Samples of cells suspected of being transformed are harvested and assayed for the presence of HIV p24 using antibodies specific for that antigen, such antibodies being well known in the art.

Thus, in addition to the transformed host cells themselves, the present invention also contemplates a culture of those cells, preferably a monoclonal (clonally homogeneous) culture, or a culture derived from a monoclonal culture, in a nutrient medium. Preferably, the culture also contains a protein displaying HIV p24 antigenicity and more preferably, water soluble HIV p24.

Nutrient media useful for culturing transformed host cells are well known in the art and can be obtained from several commercial sources.

E. Methods for Producino Recombinant HIV p24 and HIV p24-gp41 Fusion Proteins Another aspect of the present invention pertains to a method for producing recombinant HIV p24 and HIV p24-gp41 fusion proteins of this invention.

The present method entails initiating a culture comprising a nutrient medium containing host cells, preferably *E. coli* cells, transformed with a recombinant DNA molecule of the present invention that is capable of expressing a recombinant HIV p24 protein or a HIV p24-gp41 fusion protein. The culture is maintained for a time period sufficient for the transformed cells to express the recombinant HIV p24 protein or HIV p24-gp41 fusion protein. The expressed protein is then recovered from the culture.

However, as is well known in the art, the expressed protein recovered will not typically contain the amino-terminal methionine residue present on the initial translation product because of cellular processing.

Methods for recovering an expressed protein from a culture are well known in the art and include fractionation of the protein-containing portion of the culture using well known biochemical techniques. For instance, the methods of gel filtration, gel chromatography, ultrafiltration, electrophoresis, ion exchange, affinity chromatography and the like, such as are known for protein fractionations, can be used to isolate the expressed proteins found in the culture. In addition, immunochemical methods, such as immunoaffinity, immunoadsorption and the like can be performed using well known methods.

F. Recombinant HIV p24 Protein, HIV p24-gp41 Fusion Proteins and HIV p24-A5 Conjugate Compositions In another embodiment, the present invention contemplates a composition containing HIV p24 protein that is essentially free of both procaryotic antigens (i.e., host cell-specific antigens) and other HIV-related proteins.

By "essentially free" is meant that the ratio of HIV p24 protein to either procaryotic antigen or other HIV-related protein is at least 1000:1, and preferably is 10,000:1.

The presence and amount of contaminating protein in a recombinant protein preparation can be determined by well known methods. Preferably, a sample of the composition is subjected to sodium dodecy sulfate-polyacrylamide gel electrophoresis (SDS-PAGE) to separate the recombinant protein from any protein contaminants present. The ratio of the amounts of the proteins present in the sample is then determined by densitometric soft laser scanning, as is well known in the art. See Guilian et al., *Anal. Biochem.*, 129:277–287 (1983).

Preferably, the HIV p24 protein present in the composition has an amino acid residue sequence represented by FIG. 1A from residue 1 or 2 to residue 232.

A HIV p24-gp41 fusion protein is contemplated in the present invention having an amino acid residue sequence corresponding from its amino-terminus to its carboxy-terminus to the amino acid residue sequence shown in FIG. 1B from residue 1 or 2 to about residue 248, in FIG. 1C from residue 1 or 2 to about residue 249, in FIG. 1D from residue 1 or 2 to about residue 324, or in FIG. 1E from residue 1 or 2 to about residue 274. A preferred HIV p24-gp41 fusion protein has a sequence corresponding to, and more preferably identical to, the residue sequence in FIG. 1B from residue 1 or 2 to about residue 257, in FIG. 1C from residue 1 or 2 to about residue 258, in FIG. 1E from residue 1 or 2 to about residue 333, or in FIG. 1E from residue 1 or 2 to about residue 283. Also contemplated are compositions containing a HIV p24-gp41 fusion protein of this invention.

Preferred HIV antigens of the present invention have a common amino terminal portion corresponding in amino acid residue sequence to the sequence represented in FIG. 1A from residue 1 or 2 to residue 224 (i.e., a p24 derived portion), and have varying carboxy termini, preferably including an amino acid residue sequence capable of immunologically mimicking an HIV gp41 epitope. For example, preferred HIV p24-gp41 fusion proteins are represented in FIG. 6 having several contemplated carboxy termini. In preferred embodiments, the HIV p24-gp41 fusion proteins are in non-reduced form, i.e., are substantially free of sulfhydryl groups because of intramolecular Cys-Cys bonding.

In preferred compositions, the HIV p24 protein, HIV p24-gp41 fusion protein, or HIV p24-A5 conjugate as described hereinbelow, is present in a pharmaceutically acceptable carrier.

As used herein, the phrase "pharmaceutically acceptable" refers to molecular entities and compositions that do not produce an allergic or similar untoward reaction, such as gastric upset, dizziness and the like, when administered to a mammal. The pharmaceutically acceptable carrier may take a wide variety of forms depending upon the intended use of the preparation. In any case, the compositions contain at least about 0.001% to about 99%, of recombinant HIV p24 protein, HIV p24-gp41 fusion protein or HIV p24-A5 conjugate as an active ingredient, typically at a concentration of about 10 ug/ml.

As an example, a recombinant HIV p24 protein of the present invention can be utilized in liquid compositions such as sterile suspensions or solutions, or as isotonic preparations containing suitable preservatives.

A recombinant HIV p24 protein, HIV p24-gp41 fusion protein or HIV p24-A5 conjugate of the present invention can also be used in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a recombinant HIV p24 protein, HIV p24-gp41 fusion protein or HIV p24-A5 conjugate of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

A composition useful for inducing anti-p24 antibodies in a mammal can contain a HIV p24 protein, HIV p24-gp41 fusion protein or HIV p24-A5 conjugate of this invention, formulated into the composition as a neutralized pharmaceutically acceptable salt form. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, trimethylamine, 2-ethylamino ethanol, histidine, procaine, and the like.

The HIV p24 protein-, HIV p24-gp41 fusion protein- or HIV p24-A5 conjugate-containing composition is conventionally administered parenterally as by injection of a unit dose, for example. The term "unit dose" when used in reference to a composition used in the present invention refers to physically discrete units suitable as unitary dosages for humans, each unit containing a predetermined quantity of active material calculated to produce the desired therapeutic effect in association with the required carrier.

The composition is administered in a manner compatible with the dosage formulation, and in a therapeutically effective amount. The quantity to be administered depends on the subject to be treated, capacity of the subject's immune system to utilize the active ingredient, and degree of immune response desired. Precise amounts of active ingredient required to be administered depend on the judgement of the practitioner and are peculiar to each individual. However, suitable dosage ranges are of the order of one to ten micrograms of recombinant HIV p24 protein, HIV p24-gp41 fusion protein or HIV p24-A5 conjugate per kilogram body weight, depending on the route of administration. Typically, a unit dose for an adult human is from 100–200 micrograms when administered by parenteral injection.

It should be understood that in addition to the aforementioned carrier ingredients the pharmaceutical formulation described herein can include, as appropriate, one or more additional carrier ingredients such as diluents, buffers, flavoring agents, binders, surface active agents, thickness, lubricants, preservatives (including antioxidants) and the like, and substances included for the purpose of rendering the formulation isotonic with the blood of the intended recipient.

G. HIV p24-A5 Conjugate

The present invention contemplates an antigenic conjugate comprising a subject HIV p24 protein operatively linked via an amino acid residue side group to a polypeptide designated A5. Polypeptide A5 has an amino acid residue sequence represented by the formula:

Asp-Gln-Gln-Leu-Leu-Gly-Ile-Trp-Gly-Cys-Ser-Gly-Lys-Leu-Ile-Cys-Thr-Thr-Ala-Val-Pro-Trp-Asn-Cys.

Polypeptide A5 contains as its amino acid residue sequence a portion of the HIV gp41 amino acid residue sequence and, when used in an HIV p-24-A5 conjugate, also includes the cysteine (Cys) residue shown in the above formula at the carboxy terminus to facilitate operative linkage to a subject HIV p24 protein.

Methods for operatively linking polypeptides through an amino acid residue side group are well known in the art. Those methods include linking through one or more types of functional groups on various side chains and result in the respective polypeptide backbones being covalently linked (coupled) but separated by at lease one side group.

Useful side chain functional groups include epsilon-amino groups, beta- or gamma-carboxyl groups, thio (-SH) groups and aromatic rings (e.g. tyrosine and histidine). Methods for linking polypeptides using each of the above functional groups are described in Erlanger, *Method of Enzymology,* 70:85 (1980), Aurameas, et al., *Scand. J. Immunol.*, Vol. 8, Suppl. 7, 7-23 (1978) and U.S. Pat. No. 4,493,795 to Nestor et al., whose disclosures are all incorporated herein by reference. In addition, a site-directed coupling reaction, as described in Rodwell et al., *Biotech.*, 3:889-894 (1985), can be carried out so that the biological activity of the polypeptides is not substantially diminished.

Furthermore, as is well known in the art, both HIV p24 and polypeptide A5 can be used in their native form or their functional group content can be modified by succinylation of lysine residues or reaction with cysteine-thiolactone. A sulfhydryl group may also be incorporated into either polypeptide by reaction or amino functions with 2-iminothiolane or the N-hydroxysuccinimide ester of 3- (3-dithiopyridyl) propionate. The polypeptides can also be modified to incorporate spacer arms, such as hexamethylene diamine or other bifunctional molecules of similar size, to facilitate linking.

Particularly useful in forming linkages for coupling HIV p24 protein and polypeptide A5 are a large number of heterobifunctional reagents which generate a disulfide link at one functional group end and a peptide link at the other, including N-succidimidyl-3-(2-pyridyldithio) proprionate (SPDP). This reagent creates a disulfide linkage between itself and a cysteine residue in one protein and an amide linkage through an epsilon-amino group on a lysine or other free amino group in the other. A variety of such disulfide/amide forming agents are known. See for example *Immun. Rev.*, 62:185 (1982). Other bifunctional coupling agents form a thioester rather than a disulfide linkage. Many of these thioester forming agents are commercially available and include reactive esters of 6-maleimidocaproic acid, 2-bromoacetic acid, 2-iodoacetic acid, 4-(N-maleimidomethyl) cyclohexane-1-carboxylic acid and the like. The carboxyl groups can be activated by combining them with succinimide or 1-hydroxy-2-nitro-4-sulfonic acid, sodium salt. The particularly preferred coupling agent for the method of this invention is succinimidyl 4-(N-maleimidomethyl) cyclohexane-1-carboxylate (SMCC) obtained from Pierce Company, Rockford, Ill. The foregoing list is not meant to be exhaustive, and modifications of the named compounds can clearly be used.

Polypeptide A5 can be synthesized by any of the techniques that are known to those skilled in the polypeptide art. Synthetic chemistry techniques, such as a solid-phase Merrifield-type synthesis, are preferred for reasons of purity, antigenic specificity, freedom from undesired side products, ease of production and the like, and can be carried out according to the methods described in Merrifield et al., *J. Am. Chem. Soc.*, 85:2149–2154 (1963) and Houghten et al., *Int. J. Pept. Prot Res.*, 16:311–320 (1980). An excellent summary of the many techniques available can be found in J. M. Steward and J. D. Young, "Solid Phase Peptide Synthesis", W. H. Freeman Co., San Francisco, 1969; M. Bodanszky, et al., "Peptide Synthesis", John Wiley & Sons, Second Edition, 1976 and J. Meienhofer, "Hormonal Proteins and Peptides", Vol. 2, p. 46, Academic Press (N.Y.), 1983 for solid phase peptide synthesis, and E. Schroder and K. Kubke, "The peptides", Vol. 1, Academic Press (N.Y.), 1965 for classical solution synthesis, each of which is incorporated herein by reference.

H. Diagnostic Systems

A diagnostic system in kit form of the present invention includes, in an amount sufficient for at least one assay, a HIV p24 protein composition, a HIV p24-gp41 fusion protein, or a HIV p24-A5 conjugate of the present invention, as a separately packaged reagent. Instructions for use of the packaged reagent are also typically included.

"Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

In preferred embodiments, a diagnostic system of the present invention further includes a label or indicating means capable of signaling the formation of a complex containing a recombinant HIV p24 protein.

As used herein, the terms "label" and "indicating means" in their various grammatical forms refer to single atoms and molecules that are either directly or indirectly involved in the production of a detectable signal to indicate the presence of a complex. "In vivo" labels or indicating means are those useful within the body of a human subject. Any label or indicating means can be linked to or incorporated in an expressed protein, polypeptide, or antibody molecule that is part of an antibody or monoclonal antibody composition of the present invention, or used separately, and those atoms or molecules can be used alone or in conjunction with additional reagents. Such labels are themselves well-known in clinical diagnostic chemistry and constitute a part of this invention only insofar as they are utilized with otherwise novel proteins methods and/or systems.

The linking of labels, i.e., labeling of, polypeptides and proteins is well known in the art. For instance, antibody molecules produced by a hybridoma can be labeled by metabolic incorporation of radioisotope-containing amino acids provided as a component in the culture medium. See, for example, Galfre et al., *Meth. Enzymol.*, 73:3–46 (1981). The techniques of protein conjugation or coupling through activated functional groups are particularly applicable. See, for example, Aurameas, et al., *Scand. J. Immunol.*, Vol. 8 Suppl. 7:7–23 (1978), Rodwell et al., *Biotech.*, 3:889–894 (1984), and U.S. Pat. No. 4,493,795.

The diagnostic systems can also include, preferably as a separate package, a specific binding agent. A "specific binding agent" is a molecular entity capable of selectively binding a reagent species of the present invention but is not itself a protein expression product, polypeptide, or antibody molecule of the present invention. Exemplary specific binding agents are antibody molecules, complement proteins or fragments thereof, protein A, and the like. Preferably the specific binding agent can bind the recombinant protein when the protein is present as part of a complex.

In preferred embodiments the specific binding agent is labeled. However, when the diagnostic system includes a specific binding agent that is not labeled, the agent is typically used as an amplifying means or reagent. In these embodiments, the labeled specific binding agent is capable of specifically binding the amplifying agent when the amplifying means is bound to a reagent species-containing complex.

The diagnostic kits of the present invention can be used in an "ELISA" format to detect the presence or quantity of anti-HIV p24 antibodies in a body fluid sample such as serum, plasma or saliva. "ELISA" refers to an enzyme-linked immunosorbent assay that employs an antibody or antigen bound to a solid phase and an enzyme-antigen or enzyme-antibody conjugate to detect and quantify the amount of an antigen or antibody present in a sample. A description of the ELISA technique is found in Chapter 22 of the 4th Edition of *Basic and Clinical Immunology* by D. P. Sites et al., published by Lange Medical Publications of Los Altos, Calif. in 1982 and in U.S. Pat. No. 3,654,090; U.S. Pat. No. 3,850,752; and U.S. Pat. No. 4,016,043, which are all incorporated herein by reference.

Thus, in preferred embodiments, the HIV p24 protein, HIV p24-gp41 fusion protein or HIV p24-A5 conjugate of the present invention can be affixed to a solid matrix to form a solid support that is separately packaged in the subject diagnostic systems.

The reagent is typically affixed to the solid matrix by adsorption from an aqueous medium although other modes of affixation, well known to those skilled in the art can be used.

Useful solid matrices are well known in the art. Such materials include the cross-linked dextran available under the trademark SEPHADEX from Pharmacia Fine Chemicals (Piscataway, N.J.); agarose; beads of polystyrene about 1 micron to about 5 millimeters in diameter available from Abbott Laboratories of North Chicago, Ill.; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The HIV p24 protein, HIV p24-gp41 fusion protein, P24-A5 conjugate, labeled specific binding agent or amplifying reagent of any diagnostic system described herein can be provided in solution, as a liquid dispersion or as a substantially dry power, e.g., in lyophilized form. Where the indicating means is an enzyme, the enzyme's substrate can also be provided in a separate package of a system. A solid support such as the before-described microtiter plate and one or more buffers can also be included as separately packaged elements in this diagnostic assay system.

The packages discussed herein in relation to diagnostic systems are those customarily utilized in diagnostic systems. Such packages include glass and plastic (e.g., polyethylene, polypropylene and polycarbonate) bottles, vials, plastic and plastic- foil laminated envelopes and the like.

EXAMPLES

The following examples are given for illustrative purposes only and do not in any way limit the scope of the invention.

1. Production of Recombinant DNA Molecules

A. Isolation of the p24 Gene From the Gag Gene and Its Introduction Into an Expression Vector The gag region from the pHXB2CG plasmid clone of HTLV IIIB (obtained from Dr. Robert Gallo, National Cancer Institute, Bethesda, Md.) was isolated by EcoR V restriction enzyme digestion of plasmid pHXB2CG and the resulting 2.86 kilobase fragment was isolated and inserted by ligation into the EcoRV site of a modified pUC8 vector (pUC8NR) to form plasmid pUC-GAG (see step 1 of FIG. 2A).

The plasmid (pUCGAG) was mutagenized to generate an ATG translational initiation codon and an Nde I restriction enzyme site (CATATG) at the beginning of the p24 structural gene of gag by the following series of manipulations (summarized in step 2 of FIG. 2A). After transformation of pUCGAG into the methylation deficient dam- strain of E. coli, NEB, a gap was created in the pUCGAG DNA at the p24 amino terminus by cutting with the ClaI and PstI restriction enzymes to form gapped pUCGAG that lacks the smaller DNA segment from the p24 amino terminus. Ten micrograms of gapped pUCGAG DNA and 10 micrograms of pUC-GAG DNA cut with the restriction enzyme EcoR I were both subjected to electrophoresis on a 1% agarose gel, and the DNA fragments were each separately isolated from the agarose gel by electroelution (using a model 1750 sample concentrator from ISCO, Lincoln, Nebr.), combined, extracted twice with a 50/50 mixture of phenol and chloroform, and precipitated with the addition of sodium acetate (final concentration, 100 mM) and three volumes of ethanol.

The precipitated DNAs were collected by centrifugation and resuspended to a concentration of 25 micrograms per milliliter in water. After addition of an equal volume of annealing buffer (80% formamide, 100 mM Tris, pH 8.0, 25 mM EDTA) the resuspended DNAs were denatured by boiling for 5 minutes and allowed to anneal at 37° C. for 30 minutes. The annealed DNAs were diluted with an equal volume of water and precipitated in ethanol as described above to form precipitated annealed DNA.

The Nde I and ATG sequences were operatively linked to the amino terminus of the p24 gene using the following synthetic oligonucleotide:

The 10 nucleotides at the 5' end and 9 nucleotides at the 3' end of this oligonucleotide are homologous to the HTLV IIIB DNA sequence (University of Wisconsin genetic database). The intervening nucleotides were chosen to minimize the formation of secondary structures within the oligonucleotide and within the RNA expected to be generated from this sequence during expression of these sequences in E. coli.

Forty picomoles of the above oligonucleotide (synthesized on a Pharmacia Gene Assembler) was phosphorylated (as described in Molecular Cloning by T. Maniatis, E. F. Fritsch and J. Sambrook, Cold Spring Harbor Laboratory, 1982, p. 125) and admixed with 2.5 micrograms of the precipitated annealed DNA described above. The admixed DNAs were then annealed by heating the admixture to 65° C. for 5 minutes and then cooling to room temperature over the course of an hour in ligase buffer (op. cit., p. 474). The resulting DNA molecule (i.e., a gapped template) containing the precipitated annealed DNA described above and the gapped template with the annealed oligonucleotide was then repaired in vitro in ligase buffer by incubating for 3 hours at 15° C. in the presence of 25 micromolar of each deoxynucleoside triphosphate, 50 micromolar adenosine triphosphate and 5 units of T4 DNA ligase and 1 unit of the Klenow fragment of E. coli DNA polymerase.

After transformation into competent cells of the JM83 strain of E. coli the bacterial colonies were screened by hybridization to radiolabelled oligonucleotide after lifting the colonies onto nitrocellulose (op. cit.,pp. 250-251, 313-329). A single colony was isolated by this procedure which gave the following plasmid DNA sequence for the amino terminal sequence of the p24 gene (pUCp40, FIG. 2A):

Met Pro Ile Val . . .

5' taccat ATG CCA ATC GTG . . .3'.

The DNA fragment from pUCp40 encoding a p24-p15 fusion protein referred to as p40 below and located between the Nde I restriction enzyme site created by the above mutagenesis and the EcoRV site on the carboxy terminal side of the gag gene, was isolated by first digesting plasmid pUCp40 with Nde I and EcoR V followed by separation on agarose gels, extraction and precipitation of the separated fragment.

Plasmid pGEX7 DNA was linearized by digestion with Nde I and EcoR V. Plasmid pGEX7 is a bacterial expression vector deposited as plasmid PHAGE 38 with the American Type Culture Collection (ATCC) on Jun. 9, 1988 and given the ATCC accession number 40464.

It contains a lambda bacteriophage promoter (P$_L$), the gene for its temperature sensitive repressor (CI 857), a consensus bacterial ribosome binding site and an origin of replication (ori).

The digestion of pGEX7 with Nde I and EcoR V results in the production of two linear fragments, one of which contains the amp' and CI857 genes and the origin of replication and has Nde I and EcoR V cohesive termini. The above described p40 gene-containing Nde I/EcoR V restriction fragment of pUCp40 was then ligated to the pGEX7 Nde I/EcoR V amp' gene-containing fragment via their respective Nde I and EcoR V termini to form the plasmid pGEXp40. (Step 3, FIG. 2A.)

The sequences of pGEXp40 encoding p15 were removed from plasmid pGEXp40 by restriction digestion with the enzymes PpuM I and BamH I. Thereafter the 3' end of the p24 gene was reconstructed as is summarized by step 4 in FIG. 2A by incorporating the two following synthetic oligonucleotides (synthetic linker) containing the PpuM I and BamH I restriction enzyme sites and translational stop codons:

5'
GACCCGGCCATAAGGCAAGAGTTTT-
GTAATAAG 3'

3'
GGCCGGTATTCCGTTCTCAAAACAT-
TATTCCTAG 5'.

The resulting rDNA plasmid (pGEXp24) encodes the following sequence at the carboxy terminal end of p24:

Pro Gly His Lys Ala Arg Val Leu * *

5' GA CCC GGC CAT AAG GCA AGA GTT
TTG TAA TAA G 3'.

Thus, rDNA plasmid pGEXp24 contains first and second double stranded DNA segments operatively linked via Nde I and BamH I cohesive termini present on both segments. The first segment contains the recombinant HIV p24 protein structural gene and has a nucleotide base sequence represented by FIG. 1A from base 15 at its Nde I terminus (5' coding strand terminus) to base 718 at its BamH I terminus (3' coding strand terminus). The second segment is the expression vector and is the ampicillin resistance (amp') gene-containing Nde I/BamH I restriction fragment of pGEX7.

B. Production of A Structural Gene Coding For A Fusion Protein pGEXp24gp41: The plasmid pGEXp24, produced in Example 1A, was digested with the restriction enzyme PpuM I to form a linearized pGEXp24 DNA segment having PpuM I cohesive termini. A DNA segment having PpuM I cohesive termini and coding for an amino acid residue sequence capable of immunologically mimicking an HIV gp41 epitope (polypeptide A5) was ligated to the linearized pGEXp24 DNA to form the recombinant DNA plasmid pGEXp24gp41. As a result of the ligation, plasmid pGEXp24gp41 contains the HIV p24-gp41 fusion protein (p24-A5) structural gene defined by the nucleotide base sequence as shown in FIG. 1B from base 16 to base 786. That is, pGEXp24gp41 is a plasmid containing first and second double stranded DNA segments operatively linked via Nde I and BamH I cohesive termini present on both segments. The first segment contains the HIV p24-gp41 fusion protein encoding structural gene and has the nucleotide base sequence represented by FIG. 1B from base 15 at its Nde I terminus (5' coding strand terminus) to base 793 at its Bam HI terminus (3' coding strand terminus). The second segment is the amp' gene-containing Nde I/BamH I restriction fragment of plasmid pGEX7. The HIV p24-gp41 fusion protein structural gene is operatively linked to the pGEX7 expression control elements, e.g., the lambda promoter, and is therefore expressed when a compatible bacterial host is transformed with pGEXp24gp41.

pGEXp24gp41-2: A linearized pGEXp24 DNA segment having PpuM I cohesive termini was prepared as described above for pGEXp24gp41. A DNA segment having PpuM I cohesive termini and coding for an amino acid residue sequence capable of immunologically mimicking an HIV type 2 (HIV-2) epitope (polypeptide A2) was ligated to the linearized pGEXp24 DNA to form the recombinant plasmid pGEXp24gp41-2. As a result of the ligation, plasmid pGEXp24gp41-2 contains the HIV p24-gp41-2 fusion protein (p24-A2) structural gene defined by the nucleotide base sequence as shown in FIG. 1C from base 16 to base 789. That is, pGEXp24gp41-2 is a plasmid containing first and second double stranded DNA segments operatively linked via Nde I and BamH I cohesive termini present on both segments. The first segment contains the HIV p24-gp41-2 fusion protein encoding structural gene and has the nucleotide base sequence represented by FIG. 1C from base 15 at its Nde I terminus (5' coding strand terminus) to base 796 at its BamH I terminus (3' coding strand terminus). The second segment is the amp' gene-containing Nde I/BamH I restriction fragment of plasmid pGEX7. The HIV p24-gp41-2 fusion protein structural gene is operatively linked to the pGEX7 expression control elements, e.g., the lambda promoter, and is therefore expressed when a compatible bacterial host is transformed with pGEXp24gp41-2.

C. Production of a Structural Gene Coding for a Fusion Protein Containing Polypeptide Repeats pGEXp24gp41-1,2,1,1: Plasmids pGEXp24gp41 and pGEXp24gp41-2, prepared in Example 1B, were each separately digested to completion with the restriction enzyme Ava II, producing in each case a double stranded DNA segment having Ava II cohesive ends and each coding for an amino acid residue sequence capable of immunologically mimicking an HIV gp41 epitope, identified herein as polypeptides A5 and A2, respectively. The polypeptide A5- or polypeptide A2-coding DNA segments were each subjected to electrophoresis on polyacrylamide gel electrophoresis, and the DNA segments were each separately isolated from the gel by electroelution and precipitated as described in Example 1A.

The precipitated DNA segments that code for polypeptides A5 and A2 were admixed with the PpuM I linearized pGEXp24 DNA segment prepared above and the three admixed DNA segments were ligated to form plasmids having a variety of combinations of input segments as is possible with ligation of three DNA segments all having the same cohesive ends. The formed plasmids were transformed into E. coli and were each individually isolated as before. Isolated plasmids were then characterized by restriction enzyme digestion and electrophoresis on 1% agarose. Plasmids digested with Pvu II were cleaved in the pGEXp24 DNA portion once, were cleaved in the DNA segments that code for polypeptide A5 once, but were not cleaved in the DNA segments that code for polypeptide A2. Plasmids digested with HpA I cleaved if they contain a DNA segment that codes for polypeptide A2. Plasmids containing DNA segments that code for polypeptide A5, A2 or both were selected on the basis of their cleavage pattern and isolated as before. The nucleic acid base sequence was then determined for each of the isolated plasmids using the Sanger dideoxy sequencing method to verify the structure of the combined DNA segments present in each formed plasmid.

One formed plasmid, pGEXp24gp41-1,2,1,1, contains the HIV p24-gp41-1,2,1,1 fusion protein (p24-A5-A2-A5-A5) structural gene defined by the nucleotide base sequence as shown in FIG. 1D from base 16 to base 1014. That is, pGEXp24gp41-1,2,1,1 is a plasmid containing first and second double stranded DNA segments operatively linked via Nde I and BamH I cohesive termini present on both segments. The first segment contains the HIV p24-gp41-1,2,1,1 fusion protein encoding structural gene and has the nucleotide base sequence represented by FIG. 1B from base 15 at its Nde I terminus (5' coding strand terminus) to base 1021 at its BamH I terminus (3' coding strand terminus). The second segment is the amp$^r$ gene-containing Nde I/BamH I restriction fragment of plasmid pGEX7. The HIV p24-gp41-1,2,1,1 fusion protein structural gene is operatively linked to the pGEX7 expression control elements, e.g., the lambda promoter, and is therefore expressed when a compatible bacterial host is transformed with pGEXp24gp41-1,2,1,1 pGEXp24gp41-1,2: Plasmid pGEXp24gp41-2, prepared in Example 1B, was digested to completion with the restriction enzymes Hpa I and BamH I, producing two double stranded DNA segments having Hpa I and BamH I cohesive ends. The smaller of the two DNA segments was isolated from the digestion mixture by gel electrophoresis, electroelution and precipitation as described in Example 1A.

Plasmid pGEXp24gp41-1,2,1,1, prepared in Example 1C, was similarly digested with Hpa I and BamH I, and the larger of the two resulting DNA segments was similarly isolated. The small DNA segment isolated from pGEXp24gp41-2 and the large DNA segment isolated from pGEXp24gp41-1,2,1,1 were admixed in an equimolar ratio and ligated to form plasmid pGEXp24gp41-1,2 having one of each DNA segment in the produced plasmid.

The ligated plasmid was transformed into *E. coli*, individually isolated, and characterized by restriction enzyme digestion and electrophoresis as before. Plasmid pGEXp24gp41-1,2,1,1 contains the HIV p24-gp41-1,2 fusion protein (p24-A5-A2) structural gene defined by the nucleotide base sequence as shown in FIG. 1E from base 16 to base 864. That is, pGEXp24gp41-1,2 is a plasmid containing first and second double stranded DNA segments operatively linked via Nde I and BamH I cohesive termini present on both segments. The first segment contains the HIV p24-gp41-1,2 fusion protein encoding structural gene and has the nucleotide base sequence represented by FIG. 1B from base 15 at its Nde I terminus (5' coding strand terminus) to base 793 at its BamH I terminus (3' coding strand terminus). The second segment is the amp$^r$ gene-containing Nde I/BamH I restriction fragment of plasmid pGEX7. The HIV p24-gp41-1,2 fusion protein structural gene is operatively linked to the pGEX7 expression control elements, e.g., the lambda promoter, and is therefore expressed when a compatible bacterial host is transformed with pGEXp24gp41-1,2.

Other HIV-related p24-gp41 fusion protein structural genes were prepared having other combinations of polypeptide A5, and still further combinations of polypeptide A5 and polypeptide A2 can be prepared, using the methods described above for pGEXp24gp41-1,2,1,1. For example, recombinant DNA plasmids were prepared having the general designation pGEXp24gp41-X, where -X is -1,1, -1,1,1, or -1,1,1,1,1, corresponding to the fusion proteins p24-A5-A5, p24-A5-A5-A5, or p24-A5-A5-A5, respectively.

2. Recombinant Generation of Structural Gene Products

A. Recombinant HIV p24 Protein Structural Gene Expression

Plasmids containing the lambda promoter (pL) are normally carried in a strain of bacteria containing a lysogen of bacteriophage lambda in order to minimize the expression of the gene product of interest during the manipulation of DNAs. The pGEX7-based plasmids described in Example 1 were all carried in a lysogen of the MM294 strain of *E. coli*. Expression from the lambda promoter of pGEX7 can be demonstrated by transfer of the plasmid into an uninfected bacterial host (e.g., *E. coli* strain W3110 available from the American Type Culture Collection, Rockville, Md., as ATCC #27325) and inactivation of the cI repressor protein at 42° C. The pGEXp24 plasmid in W3110 was grown overnight in Luria Broth (GIBCO Laboratories, Grand Island, N.Y.) containing 50 micrograms/milliliter ampicillin at 30° C., and diluted 1/100 into fresh broth the next morning. After reaching an optical density of 0.5 at 550 nanometers the culture was shifted to a 42° C. waterbath with continuous vigorous shaking. The density of the culture was measured at various time points and a sample of cells removed for analysis of the expression of bacterial proteins by electrophoresis on a discontinuous pH sodium dodecyl sulfate/polyacrylamide gel (SDS-PAGE). An example of this type of analysis for expression of p24 is shown in FIG. 3. From the level of protein stained by Coomassie brilliant blue it appears that p24 comprises between 10% and 20% of total cellular protein after induction for 2 hours at 42° C.

Analysis of the level of p24 produced in these bacteria using the HTLV III antigen test produced by Abbott Laboratories indicates that p24 is made at $4.3 \times 10^8$ antigen units per milligram of bacterial protein (as determined by Lowry assay).

B. Expression of The Structural Gene Coding For The HIV p24-gp41 Fusion Protein

*E. coli* strain W3110 transformed with pGEXp24gp41 were induced and cultured as described in Example 2A. The recombinantly produced p24-gp41 fusion protein was isolated from the transformed cell culture as described below.

3. Purification and Analysis of Recombinant HIV p24 Protein Expressed in *E. coli*

The purification of recombinant HIV p24 was performed at 4° C. All buffers were prepared at room temperature and cooled to 4° C. before use. Tris buffers were prepared from Tris base (tris[hydroxymethyl]aminomethane), and adjusted to the appropriate pH with HCl. The protein concentration of the recombinant HIV p24 protein composition was determined using an extinction coefficient of 1.29 optical density units·cm$^{-1}$ for a 0.1% solution as calculated from the theoretical amino acid composition (D. B. Wetlaufer, Adv. Protein Chem., 1962, 17:303-390). The purity of the p24 composition was evaluated by Coomassie brilliant blue R-250 staining of samples subjected to SDS-PAGE (12.5% acrylamide) according to the procedure of Laemmli (Nature, 1971, 227:680-685).

A. Cell Lysis and Centrifugation

E. coli (W3110) cells (17 g) transformed with pGEXp24 prepared as described in Example 1A were suspended in 85 ml of a buffer containing 0.1 M sodium phosphate (prepared from NaH$_2$PO$_4$ and adjusted to pH 7.0 with NaOH), 5 mM EDTA, 5 mM benzamidine-HCl, 0.5 mM phenylmethylsulfonyl fluoride, and 1×10$^{-7}$ M pepstatin A (Sigma Chemical Co., St. Louis, Mo.). The suspension was passed twice through a French pressure cell press (catalog no. FA073, SLM Instruments Inc. Urbane, Ill.) at 16,000 psi, and the resulting homogenate was subjected to centrifugation (18,000×g, 40 min). The supernatant (79 ml) from the centrifugation was collected and centrifuged again at 100,000×g for 1 h in a L7-55 ultracentrifuge using a type 70.1 ti rotor (Beckman Instruments, Fullerton, Calif.). At this stage the recombinant HIV p24 protein is soluble and remains in the supernatant.

B. Ammonium Sulfate Precipitation

Solid ammonium sulfate to 30% saturation was then admixed to the supernatant (75 ml) from the ultracentrifugation, and following dissolution of the salt, the solution was allowed to stir for 30 min. The suspension was subjected to centrifugation at 12,000×g for 20 min. The resulting pellet was dissolved in 15 ml of a buffer containing 100 mM Tris-HCl (pH 8.5). This solution was dialyzed for 5 h against 4 l of a buffer containing 25 mM Tris-HCl (pH 8.0).

C. Anion Exchange Chromatography

The dialysate was applied (1 ml/min) to a column (2.5×18 cm) of DEAE Sepharose equilibrated with 25 mM Tris-HCl, pH 8.0 (Pharmacia, Piscataway, N.J.). Following application of sample, the column was washed (2 ml/min) with 5 column volumes of the equilibration buffer. The recombinant p24 was eluted from the column with 50 mM NaCl in the equilibration buffer (2 ml/min). The pH of the eluent from the anion exchange column that contained p24 (67.4 mg) was adjusted to 6.8 with solid NaH$_2$PO$_4$, and recombinant p24 was precipitated through the addition of solid ammonium sulfate to 30% saturation. Following dissolution of salt, the solution was stirred for 30 min, and the recombinant p24-containing precipitate was collected by centrifugation (12,000×g, 30 min).

D. Gel Filtration

The ammonium sulfate precipitate was dissolved in 10 ml of 100 mM Tris-HCl, pH 8.5, and subjected to chromatography (0.5 ml/min) on a column (2.5×90 cm) of Sephacryl S-200 (Pharmacia) previously equilibrated with buffer containing 50 mM Tris-HCl and 200 mM NaCl (pH 8.0). The fractions (4 ml) containing recombinant p24 were pooled (44 ml) and subjected to analysis by SDS-PAGE (FIG. 4). No contaminant materials were visualized after Coomassie staining of gel lanes charged with 12 and 24 micrograms of protein, respectively (FIG. 4). Subsequent storage of the essentially pure recombinant HIV p24 protein was done at −20° C.

E. Western Blotting

To confirm the expression of recombinant HIV p24 protein in E. coli transformed with pGEXp24 rDNA, the cellular proteins, including recombinant p24 protein, separated by 12.5% SDS-PAGE in Example 2 were subjected to analysis using the Western blot technique. See Towbin et al., Proc. Natl. Acad. Sci. USA. 75:4350-4354 (1979).

Briefly, the proteins were electrophoretically transferred from the SDS-PAGE gel to nitrocellulose. The resulting blot (solid-phase affixed antigen) was then immunoreacted with a 1:100 dilution of an HIV core antigen-positive serum from an AIDS patient.

The results of this Western blot analysis, shown in FIG. 5, indicate that immunoreactive recombinant HIV p24 protein was produced at detectable levels in transformed E. coli 30 minutes after induction of expression by heat inactivation of the cI repressor protein.

4. Purification of Recombinant HIV p24-gp41 Protein from E. coli

The purification of HIV p24-gp41 fusion protein p24-A5 was performed at 4° C. All buffers were prepared at room temperature and cooled to 4° C. before use. Tris buffers were prepared from Tris base, and adjusted to the appropriate pH with Hcl. Isolated p24-A5 was quantitated using an extinction coefficient of 1.56 optical density units·cm$^{-1}$ for a 0.1% solution as calculated from the theoretical amino acid composition (D. B. Wetlaufer, Adv. Protein Chem., 1962, 17:303-390). Purity of p24-A5 was evaluated by Coomassie blue staining of samples subjected to SDS polyacrylamide gel electrophoresis (12.5% acrylamide) according to the procedure of Laemmli (Nature, 1971, 227:680-685).

A. Cell lysis and centrifuqation

E. coli (W3110) cells (16 g) transformed with pGEXp24gp41 prepared as described in Example 1B were suspended in 80 ml of a buffer containing 0.1 M sodium phosphate (prepared from NaH$_2$PO$_4$ and adjusted to pH 7.0 with NaOH), 5 mM EDTA, 5 mM benzamidine-HCl, 0.5 mM phenylmethylsulfonyl fluoride (PMSF), and 1×10$^{-7}$ M pepstatin A (Sigma Chemical Co.). The suspension was passed twice through a French pressure cell press (SLM Instruments Inc., cell catalog no. FA073) at 16,000 psi, and the resulting homogenate was subjected to centrifugation (18,000×g, 40 min). The pellet (2.4 g) from the centrifugation was retained and resuspended in 50 ml of PEB buffer containing 0.1 M sodium phosphate (pH 7.0), 5 mM EDTA, and 5 mM benzamidine-HCl. The suspension was subjected to centrifugation as above. The resulting pellet (1.7 g) was resuspended in 80 ml of a buffer containing 50 mM Tris-Hcl, 3 M urea, 0.5 mM PMSF and 1×10$^{-5}$ M pepstatin A (pH 8.5). The suspension was stirred at 4° C. for 14 hours and then subjected to centrifugation as above. The supernatant was collected and dialyzed against 2 liters of a buffer containing 25 mM Tris-Hcl (pH 7.8) for 3 hours and then was subjected to centrifugation at 100,000×g for 1 hour in a Beckman L7-55 ultracentrifuge (type 70.1 Ti rotor).

B. Cation Exchange Chromatography

The supernatant produced from the ultracentrifugation of Example 4A was collected and the pH adjusted to 5.0 with 2 M acetic acid. The material was then dialyzed (two times) against 2 liters of 25 mM sodium acetate (pH 5.0). The dialysate was applied (1 ml/min) to a column (2.5×15 cm) of CM Sepharose (Pharmacia; equilibrated with 25 mM sodium acetate, pH 5.0). Following application of sample, the column was washed (2 ml/min) with 5 column volumes of the equilibration buffer. The HIV p24-gp41 fusion protein was eluted from the column with a linear gradient of NaCl in the equilibration buffer (1 liter, 0 to 400 mM in NaCl). The fractions containing the fusion protein at a purity of >95% (as determined through SDS PAGE) were pooled and stored at −80° C.

5. Preparation of a Recombinant HIV p24 Protein-Antigenic HIV gp41 Polypeptide Connjugate Three ml of the essentially pure recombinant HIV p24 protein, about 0.616 mg, produced in Example 3D were dialyzed for 48 h against 3 liter of 0.2 M sodium phosphate buffer, pH 8.5, containing 1 mM MgCl. A 10 mM solution of SPDP (Pharmacia) in ethanol was prepared and had an O. D. at 280 nm of 0.045. Two hundred ul of 0.8 M NaCO was admixed to the SPDP solution and the absorbance measured after 10 minutes. The ester (activated SPDP) concentration of the thus treated SPDP solution was calculated to correspond to 9.66 mM.

To prepare the recombinant HIV p24-SPDP derivative, 2 mg of recombinant HIV p24 protein (0.0083 umol) was treated with 0.42 umol of the activated SPDP (43 ul of the above SPDP solution) at room temperature for 15 minutes. Desalting was achieved by Sephadex G-10 chromatography by applying the samples to pd 10 columns and collecting 2 ml of the effluent. The degree of substitution was calculated to approximately 3.4 moles of thiol per mole of recombinant HIV p24 protein.

To operatively link the A5 polypeptide to the thiolated recombinant HIV p24 protein preparation, 0.162 micromoles of the peptide were admixed with the thiolated protein (about 3.5 moles of peptide per mole of p24 polypeptide) and the admixture was incubated (maintained) at 4 degrees over night. After continuing the incubation at room temperature (about 20° C.) for 8 hours, the absorbance of the solution at 343 nanometers was measured and determined to be 0.35, indicating that 3.8 moles of the thiolated p24 had hydrolyzed to yield recombinant HIV p24-A5 polypeptide conjugate (p24-A5 conjugate).

As a control, BSA-A5 conjugate was prepared by the above procedures using bovine serum albumin (BSA) in place of recombinant HIV p24 protein.

6. Enzyme-Linked Immunosorbant Assay (ELISA)

Antigens were adsorbed onto washed plastic microliter wells (Nunc MicroWell Module, catalog no. 468667). Solutions containing the antigens p24, p24-A5 fusion protein, p24-A5 conjugate or BSA-A5 conjugate, prepared in Examples 3, 4, 5 and 5, respectively, at 10 micrograms per milliliter in 50 millimolar (mM) sodium carbonate, pH 9.5 and 150 mM NaCl were admixed into the wells and maintained for one hour at room temperature. The coating solution was removed and the nonspecific binding sites on the wells were blocked by incubation overnight at room temperature with a solution of 3% bovine serum albumin (BSA, Fraction V, SIGMA Chemicals) in a phosphate-buffered saline solution (PBS: 40 g NaCl, 1 g $KH_2PO_4$, 5.7 g $Na_2HPO_4$, 1 g KCl, 1 g $NaN_3$ in 5 liters of aqueous solution). After blocking, the plate was rinsed three times with water and allowed to dry, thereby forming a blocked solid-phase affixed antigen.

ELISA assays were performed by admixing dilutions of AIDS patient serum, normal human serum or rabbit antisera directed against purified HIV recombinant p24 protein with the solid-phase affixed antigens. Sera were diluted in PBS containing 0.05% Tween 20 detergent and 0.1% BSA (PTB buffer). After maintaining the immunoreaction admixtures for one hour at 37° C. to permit immunoreaction product formation, the wells were washed three times with PBS/0.05% Tween 20. To each well was then admixed a 1:1000 dilution, in PTB buffer, of either goat anti-human IgG coupled to alkaline phosphatase (SIGMA no. A-3150) as a label or sheep anti-rabbit immunoglobulin coupled to betagalactosidase (Pharmacia) as a label. After incubation for 30 min at 37° C. with the second antibody the wells were washed five times with PBS containing 0.05% Tween 20 when alkaline phosphatase was used as a label, paranitrophenyl phosphate (SIGMA) in a buffer of 10% triethanolamine, pH 9.8, 1 mM $MgCl_2$ was admixed to each well, and the wells maintained for 30 min at room temperature. When betagalactosidase was used as a label, four micrograms per milliliter ortho-nitrophenyl galactoside (SIGMA) in 100 mM phosphate buffer, pH 7 were admixed to each well, and the wells were maintained for 2 hours at 37° C. The extent of enzymatic reaction was monitored by reading the optical density of the solution in the microwells at 405 nanometers in a BioRad spectrophotometer.

The results of these studies are shown in Table 1.

TABLE 1

ELISA Results Using Recombinant HIV p24 Protein, HIV p24-gp41 Fusion Protein and HIV p24-gp41 Conjugate

| Serum[1] Sample | Antigen[2] | | | |
|---|---|---|---|---|
| | p24 | p24-A5 fusion | p24-A5 conjugate | BSA-A5 conjugate |
| Normal | 1:80 | 1:160 | 1:320 | 1:40 |
| 13690 | 1:80 | 1:10240 | 1:5120 | 1:5120 |
| F666-4 | 1:80 | 1:10240 | 1:10240 | 1:10240 |
| F666-6 | 3:00 | 1:80 | 1:80 | 1:40 |
| 8015 | 1:80 | 1:20480 | 1:10240 | 1:10240 |
| 8036 | 1:80 | 1:10240 | 1:10240 | 1:10240 |
| 8055 | —[3] | — | — | 1:40 |
| 8057 | 1:80 | 1:10240 | 1:10240 | 1:10240 |
| rabbit anti-p24 | — | 1:64000 | 1:64000 | — |

[1]Serum samples were initially diluted 1:20 and subsequently diluted two-fold serially. An endpoint for the titration of the antisera is given where the optical density reading dropped below 0.1. Normal = serum from a healthy heterosexual human. Rabbit anti-p24 = serum from a rabbit immunized with recombinant HIV p24 protein.
[2]Solid-phase affixed antigens were: recombinant HIV p24 protein (p24); recombinant HIV p24-polypeptide A5 protein (p24-A5 fusion); recombinant HIV p24 protein-polypeptide A5 conjugate (p24-A5 conjugate); and bovine serum albumin-A5 conjugate (BSA-A5 conjugate).
[3]No detectable titer.

The results shown in Table 1 indicate that the recombinant HIV p24-A5 fusion protein and recombinant HIV p24-A5 conjugate were more sensitive in detecting anti-HIV antibodies than recombinant HIV p24 protein alone. In addition, in 2 out of 5 AIDS patient sera, the recombinant HIV p24-A5 fusion protein was more sensitive in detecting anti-HIV antibodies than the recombinant HIV p24-A5 conjugate or BSA-A5 conjugate. This was especially surprising in view of there being about 4 times as many HIV gp41 epitopes (A5 polypeptide) available for immunoreaction on the conjugates as compared to the fusion protein.

7. Purification of Recombinant HIV p24-gp41 Protein from E. Coli

HIV p24-gp41 fusion protein p24-A5 was also purified by a procedure similar to that in Example 4 but with the exceptions noted.

E. Coli (W3110) cells (50 gm) transformed with pGEXp24gp41 prepared as described in Example 1B were suspended with a tissue homogenizer (Polytron fitted with a 15 mm probe) in 250 ml of suspension buffer (0.1 M sodium phosphate, pH 7.0, 5 mM EDTA, 5 mM benzamidine-HCl, 0.5 mM PMSF) containing 0.17% (w/v) lysozyme (SIGMA, grade I). The suspension was maintained at 22° C. for 40 min with stirring agitation and then cooled to 4° C. The cooled suspension was then passed through a French press and centrifuged (18,000×g, 40 min). The resulting pellet (6.4 gm) was resuspended in 150 ml of PEB buffer and centrifuged (18,000×g, 30 min). The resulting pellet was resuspended in 100 ml of a buffer containing 100 mM Tris-HCl, 3 M urea and 10 mM dithiothreitol, pH 8.5. The suspension was stirred at 4° C. for 1 hr and then subjected to centrifugation for 40 min at 35,000 rpm in a 45 Ti rotor (Beckman). The resulting supernatant was collected and dialyzed against 4 liters of a buffer containing 0.1 M sodium phosphate and 30% saturated ammonium sulfate, pH 6.5, and then was subjected to centrifugation for 20 min at 18,000×g. The resulting pellet was resuspended in 35 ml of a buffer containing 0.1 M sodium phosphate, 5 mM EDTA, 6 M guanidine HCl and 10 mM mercaptoethanol, pH 7.0, to form a guanidine fusion protein solution.

The guanidine solution was applied to a column (5.0×90 cm) of Sephacryl S-200 (Pharmacia) pre-equilibrated with S-200 buffer containing 6 M guanidine HCl, 50 mM Tris, 5 mM EDTA and 10 mM mercaptoethanol, pH 7.0. Eluted fractions were collected when S-200 buffer was then applied to the column, and each fraction was monitored for absorbance at 280 nm (A280) to determine protein content. Fractions containing a peak of eluted protein were pooled and diluted to an A280 of 0.5 using a buffer containing 15 mM Tris-HCl, pH 8.5, and 3 M urea. Each pooled peak was analyzed by SDS-PAGE as described in Example 2A to identify the pooled fractions containing purified HIV p24-gp41 fusion protein. The fusion protein containing pool was dialyzed for 4 hours and then for 14 hours against 4 liters of 15 mM Tris-HCl, pH 8.5, containing 3 M urea to form a dialyzed fusion protein solution containing urea. The dialyzed solution was then dialyzed for 4 hours against 15 mM Tris-HCl, pH 8.5, to form dialyzed fusion protein, said protein being substantially free of sulfhydryl groups, i.e., the protein was in nonreduced form.

The dialyzed fusion protein was applied (2 ml/min) to a column (2.6×20 cm) of DEAE-Sepharose (Pharmacia) pre-equilibrated with 15 mM Tris-HCl, pH 8.5. Following application of sample, the column was washed (2 ml/min) with 2 column volumes of equilibration buffer containing 10 mM NaCl. The HIV p24-gp41 fusion protein was eluted from the column with a gradient of NaCl in the equilibration buffer (1 liter, 10 to 30 mM in NaCl). The fractions containing the fusion protein at a purify of greater than 95% (as determined through SDS-PAGE) were pooled to form DEAE-isolated fusion protein.

The pH of the pooled fractions from the DEAE-Sepharose column was adjusted to 5.5 by adding 20% acetic acid and was then dialyzed against 4 liters of a buffer containing 25 mM sodium acetate, pH 5.0. The dialysate was then subjected to centrifugation for 1 hr at 40,000 rpm in a type 45 Ti rotor in a Beckman L7-55 ultracentrifuge. The resulting supernatant was applied (2 ml/min) to a column (2.6×10 cm) of CM-Sepharose CL-6B (Pharmacia) pre-equilibrated with a buffer containing 25 mM sodium acetate, pH 5.0. Following application of sample, the column was washed (2 ml/min) with 200 ml of the equilibration buffer containing 30 mM NaCl. The HIV p24-gp41 fusion protein was eluted from the column with a linear gradient of NaCl in the equilibration buffer (1 liter, 30 to 250 mM in NaCl). The fractions containing the fusion protein at a purity of a greater than 95% (as determined through SAS-PAGE) were pooled and stored at −20° C. to form CM-isolated fusion protein.

8. Purification of Recombinant HIV p24-gp41-2 Protein from E. coli

HIV p24-gp41-2 fusion protein p24-A2 was purified by the procedure described in Example 7 with the following exceptions as noted.

E. coli cells were transformed with pGEXp24gp41-2, prepared as described in Example 1B. The p24-gp41-2 fusion protein expressed by the transformed cells was then isolated as described in Example 7 to form DEAE isolated protein.

9. Purification of Recombinant HIV p24-gp41-1,2 Protein from E. coli

HIV p24gp41-1,2 fusion protein p24-A5-A2 was purified by the procedure described in example 7 with the following exceptions as noted.

E. coli cells were transformed with pGEXp24gp41-1,2, prepared as described in Example 1B, and then were processed as described in Example 7 through the guanidine resuspension step to form a guanidine fusion protein solution containing isolated HIV p24gp41-1,2 fusion protein.

10. Enzyme-Linked Immunosorbant Assay (ELISA)

ELISA was conducted as described in Example 6 using the antigens p24, or one of the fusion proteins p24-A5, p24-A2, or p24-A5-A2, prepared in Examples 3, 7, 8 and 9, respectively.

The results of the ELISA studies are shown in Table 2.

TABLE 2

ELISA Results Using Recombinant HIV p24 Protein and HIV Fusion Proteins p24-gp41, p24-gp41-2 or p24-gp41-1,2

| Serum Sample[1] | Antigen[2] | | | |
|---|---|---|---|---|
| | p24 | p24-A5 fusion | p24-A2 fusion | p24-A5-A2 fusion |
| HIV-1 | | | | |
| 13690 | 1:900 | 1:8100 | 1:900 | 1:8100 |
| F666-4 | 1:400 | 1:10800 | 1:400 | 1:10800 |
| HIV-2 | | | | |
| 2A | 1:100 | 1:300 | 1:2700 | 1:2700 |
| 2B | 1:100 | 1:300 | 1:2700 | 1:2700 |
| rabbit anti-p24 | 1:81000 | 1:81000 | 1:81000 | 1:81000 |
| rabbit | —[3] | 1:9000 | — | 1:3000 |

TABLE 2-continued

ELISA Results Using Recombinant HIV
p24 Protein and HIV Fusion Proteins
p24-gp41, p24-gp41-2 or p24-gp41-1,2

| Serum Sample[1] | Antigen[2] | | | |
|---|---|---|---|---|
| | p24 | p24-A5 fusion | p24-A2 fusion | p24-A5-A2 fusion |
| anti-gp41, HIV1 rabbit | — | — | 1:1000 | 1:100 |
| anti-gp41,HIV-2 | | | | |

[1]Serum samples were initially diluted 1:100 and subsequently diluted three-fold serially. An endpoint for the titration is given where the optical density reading dropped below 0.2. Samples 13690 and F666-4 were obtained from AIDS patients having confirmed HIV-1 infection, and samples 2A and 2B were obtained from AIDS patients having confirmed HIV-2 infection. Rabbit anti-p24 = serum from a rabbit immunized with recombinant p24, rabbit anti-gp41, HIV-1 = serum from a rabbit immunized with A5 peptide conjugated to BSA, rabbit anti-gp41, HIV-2 = serum from a rabbit immunized with A2 peptide conjugated to BSA.
[2]Solid-phase affixed antigens were: recombinant HIV p24 protein (p24); recombinant HIV p24-polypeptide A5 protein (p24-A5 fusion); recombinant HIV p24-polypeptide A2 protein (p24-A2 fusion); recombinant HIV p24-polypeptide A5 and A2 protein (p24-A5-A2 fusion).
[3]No detectable titer.

The results in Table 2 indicate that recombinant HIV fusion proteins p24-A5, p24-A2 and p24-A5-A2 were more sensitive in detecting anti-HIV antibodies than recombinant p24 protein alone. In addition, type specificity is demonstrated by the more sensitive detection of anti-HIV-1 antibodies using fusion proteins that contain the A5 polypeptide when compared to fusion protein that contains the A2 polypeptide. Similarly, increased sensitivity was observed for detecting anti-HIV-2 antibodies using fusion proteins that contain the A2 polypeptide when compared to fusion protein that contains the A5 polypeptide.

The foregoing description and the examples are intended as illustrative and are not to be taken as limiting. Still other variations within the spirit and scope of this invention are possible and will readily present themselves to those skilled in the art.

What is claimed is:

1. A DNA segment comprising a first nucleotide base sequence operatively linked at its 3' terminus to the 5' terminus of a second nucleotide base sequence, said first sequence having a nucleotide base sequence represented by the formula:

AGGAGGGTTTTTCAT, and said second sequence having a nucleotide base sequence encoding amino acid residues of a recombinant HIV p24 protein as shown in FIG. 1A, from amino acid residue 1 through amino acid residue 232, or as shown in FIG. 1B, from amino acid residue 1 through amino acid residue 225.

2. The DNA segment of claim 1 wherein said second sequence encodes an amino acid residue sequence represented by FIG. 1A from residue 1 to residue 232.

3. The DNA segment of claim 2 wherein said segment has a nucleotide base sequence represented by FIG. 1A from base 1 to base 711.

4. A DNA segment comprising a first nucleotide base sequence operatively linked in frame at its 3' terminus to the 5' terminus of a second nucleotide base sequence, said first nucleotide base sequence having a nucleotide base sequence represented by the formula:

AGGAGGGTTTTTCAT, and said second nucleotide base sequence having a nucleotide base sequence encoding an amino acid residue sequence represented by the amino acid residue sequence shown in FIG. 1B from amino acid residue 1 to amino acid residue 257, FIG. 1C from amino acid residue 1 to amino acid residue 258, or FIG. 1E from amino acid residue 1 to amino acid residue 283.

5. A DNA segment comprising a first nucleotide base sequence operatively linked in frame at its 3' terminus to the 5' terminus of a second nucleotide base sequence, said first nucleotide base sequence having a nucleotide base sequence represented by the formula:

AGGAGGGTTTTTCAT, and said second nucleotide base sequence having a nucleotide base sequence represented by the nucleotide base sequence shown in FIG. 1B from base 16 to base 786, FIG. 1C from base 16 to base 789, or FIG. 1E from base 16 to base 864.

6. A recombinant DNA molecule comprising a vector having a prokaryotic promoter operatively linked in frame to a DNA segment, said segment comprised of a first nucleotide base sequence operatively linked in frame at its 3' terminus to the 5' terminus of a second nucleotide base sequence, said first sequence having a nucleotide base sequence represented by the formula:

AGGAGGGTTTTTCAT, and said second sequence having a nucleotide base sequence encoding amino acid residues of a recombinant HIV p24 protein as shown in FIG. 1A, from amino acid residue 1 through amino acid residue 232, or as shown in FIG. 1B, from amino acid residue 1 through amino acid residue 225.

7. The recombinant DNA of claim 6 wherein said second sequence encodes an amino acid residue sequence represented by FIG. 1A from residue 1 to residue 232.

8. The recombinant DNA of claim 7 wherein said second sequence has a nucleotide base sequence represented by FIG. 1A from base 1 to base 711 or 718.

9. A recombinant DNA molecule comprising a vector having a prokaryotic promoter operatively linked in frame to a DNA segment, said DNA segment comprised of a first nucleotide base sequence operatively linked in frame at its 3' terminus to the 5' terminus of a second nucleotide base sequence, said first sequence having a nucleotide base sequence represented by the formula:

AGGAGGGTTTTTCAT, and said second sequence defining structural gene coding for a HIV p24-gp41 fusion protein having an amino acid residue sequence represented by the amino acid residue sequence shown in FIG. 1B from amino acid residue 1 to amino acid residue 257, FIG. 1C from amino acid residue 1 to amino acid residue 258, or FIG. 1E from amino acid residue 1 to amino acid residue 283.

10. A recombinant DNA molecule comprising a vector having a prokaryotic promoter operatively linked in frame to a DNA segment, said DNA segment having a nucleotide base sequence represented by the nucleotide base sequence shown in FIG. 1B from base 1 to base 793, FIG. 1C from base 1 to base 796, or FIG. 1E from base 1 to base 871.

11. A recombinant DNA molecule selected from the group consisting of pGEXp24gp41, pGEXp24gp41-2, and pGEXp24gp41-1,2.

12. A transformed cell culture comprising a nutrient medium containing a procaryotic host cell transformed with a recombinant DNA molecule according to any of claims 6, 9 or 10.

* * * * *